US012708706B2

(12) United States Patent
Kim

(10) Patent No.: US 12,708,706 B2
(45) Date of Patent: Aug. 18, 2026

(54) AUXILIARY APPARATUS FOR FECAL BYPASS

(71) Applicant: JSR MEDICAL CO., LTD, Daegu (KR)

(72) Inventor: Jae Hwang Kim, Daegu (KR)

(73) Assignee: JSR MEDICAL CO., LTD., Daegu (KR)

( * ) Notice: Subject to any disclaimer, the term of this patent is extended or adjusted under 35 U.S.C. 154(b) by 981 days.

(21) Appl. No.: 17/913,622

(22) PCT Filed: Mar. 12, 2021

(86) PCT No.: PCT/KR2021/003063

§ 371 (c)(1),
(2) Date: Sep. 22, 2022

(87) PCT Pub. No.: WO2021/194139

PCT Pub. Date: Sep. 30, 2021

(65) Prior Publication Data

US 2023/0173164 A1 Jun. 8, 2023

(30) Foreign Application Priority Data

Mar. 25, 2020 (KR) ........................ 10-2020-0036293

(51) Int. Cl.
*A61M 3/02* (2006.01)
*A61F 5/442* (2006.01)

(52) U.S. Cl.
CPC ........... *A61M 3/0283* (2013.01); *A61F 5/442* (2013.01); *A61M 3/0295* (2013.01); *A61M 2202/068* (2013.01)

(58) Field of Classification Search
CPC ............. A61F 5/442; A61M 2202/068; A61M 2210/106; A61M 2210/1064;

(Continued)

(56) References Cited

U.S. PATENT DOCUMENTS 5,312,343 A * 5/1994 Krog .................. A61M 25/1011
604/101.03
8,398,669 B2 * 3/2013 Kim .......................... A61F 2/04
604/101.01

(Continued)

FOREIGN PATENT DOCUMENTS

JP 2005519709 A 7/2005
JP 2014504915 A 2/2014

(Continued)

OTHER PUBLICATIONS

JP Office Action for corresponding JP Application No. 2022-555136, dated Sep. 4, 2023, pp. 1-8.

(Continued)

*Primary Examiner* — Shefali D Patel

(74) *Attorney, Agent, or Firm* — Renner Otto Boisselle & Sklar LLP; Christopher P. Harris

(57) ABSTRACT

Disclosed is an auxiliary apparatus for fecal bypass for bypassing and discharging feces in intestines. Since supporting portions are connected to a single air flow tube to simultaneously expand when air is injected, and a size of the supporting portions is limited, the auxiliary apparatus for fecal bypass does not damage an inner wall and an outer wall (e.g., a mucous membrane and a serous membrane) of the intestines. Also, the auxiliary apparatus for fecal bypass comprises a liquid moving tube allowing a therapeutic liquid being refluxed quickly and automatically when a pressure inside the intestines increases, thereby preventing abdominal pain of a patient.

6 Claims, 17 Drawing Sheets

(58) Field of Classification Search
CPC .......... A61M 2210/1067; A61M 3/027; A61M 3/0283; A61M 3/0295
See application file for complete search history.

(56) References Cited

U.S. PATENT DOCUMENTS

| | | | | |
|---|---|---|---|---|
| 12,257,408 | B2 * | 3/2025 | Göbel .................. | A61M 25/04 |
| 2005/0033226 | A1 | 2/2005 | Kim | |

FOREIGN PATENT DOCUMENTS

| | | | | |
|---|---|---|---|---|
| KR | 10-2002-0028506 | A | 4/2002 | |
| KR | 10-2008-0021184 | A | 3/2008 | |
| KR | 10-2014-0022270 | A | 2/2014 | |
| KR | 10-1773520 | B1 | 8/2017 | |
| KR | 10-2018-0033983 | A | 4/2018 | |
| KR | 20180033983 | A * | 4/2018 | ........... A61F 5/0093 |
| WO | 2018216830 | A1 | 11/2018 | |

OTHER PUBLICATIONS

EESR for European application No. 21 77 6464, dated Mar. 12, 2024, 35 pages.

International Search Report and Written Opinion issued in connection with corresponding PCT Patent Application No. PCT/KR2021/003063 dated Jul. 20, 2021.

* cited by examiner

AUXILIARY APPARATUS FOR FECAL BYPASS

RELATED APPLICATIONS

The present invention is a U.S. National Stage under 35 USC 371 patent application, claiming priority to Serial No. PCT/KR2021/003063, filed on Mar. 12, 2021, which claims priority from Korean Patent Application No. 10-2020-0036293 filed on Mar. 25, 2020; the entireties of both are hereby incorporated herein by reference.

TECHNICAL FIELD

The present technology relates to an auxiliary apparatus for fecal bypass for rectal surgery patients.

BACKGROUND ART

Cancer has been the number one cause of death since 1990, and after 1995, it is counted as the overwhelming cause of death compared to other causes. Cancer ranks first as a cause of death in those in their 40s, third in their 20s, and second in their 30s. The medical industry is constantly trying to conquer cancer, and is developing reagents, treatment methods, and therapeutic devices to treat cancer.

Among cancers, colorectal cancer has been increasing continuously since the 2000s. Therefore, interest in colorectal cancer is steadily increasing. Colorectal cancer is a malignant tumor that occurs in the colon and rectum, and is adenocarcinoma most often occurs in the mucous membrane of the large intestine. In addition to adenocarcinoma, various tumors such as squamous cell carcinoma and malignant lymphoma are found, and sometimes the cancer invades the colon or metastasizes to other sites.

The current colorectal cancer treatment method is to make an incision at an upper and lower end of the lesion site, connect the normal part, and then suture the incision.

Colorectal cancer treatment itself is painful for a patient, but leakage occurring at an anastomosis site after surgery is also dangerous. Leakage of the anastomotic site may cause serious complications and threaten a patient's life. In addition, it may cause anastomotic stenosis in the long term and seriously deteriorate a patient's quality of life.

To prevent this, leakage of the anastomotic site is prevented by tying a biodegradable band to the intestine at a certain upper position from the surgical site, fixing an auxiliary apparatus for fecal bypass that may bypass feces in this area, closing a space through which the fecal bypass auxiliary apparatus may move to a lower side thereof, injecting treatment liquid, and discharging the treatment liquid into an inner space of the auxiliary apparatus for fecal bypass to bypass stool.

However, patients who use the auxiliary apparatus for fecal bypass constantly complain about the same problem when using the auxiliary apparatus for fecal bypass, so research is essential to solve this problem and the complaints. The problems customers are talking about are as below.

The first problem is stomach pain.

When the treatment liquid is injected into the patient's intestinal tract, the intestines perform peristalsis. This movement is one to move the material in the intestine toward an anus. At this time, since the auxiliary apparatus for fecal bypass closes an inside of the intestine, it increases the pressure in the intestine. The increase in intra-intestinal pressure induced abdominal pain in the patient.

The second problem is erosion of the intestinal lining

The auxiliary apparatus for fecal bypass is fixed to an inner wall of the intestine with a band fixed to an outer wall of the intestine. When the internal pressure of the intestine is increased, the auxiliary apparatus for fecal bypass fixed in the intestine pushes the inner wall of the intestine to prevent the auxiliary apparatus from being pushed in the intestine and applies pressure to the band, and as this process is repeated, the inner wall of the intestine is damaged. Such damage to the intestinal lining may lead to serious complications such as intestinal perforation, peri-intestinal abscess, and sepsis.

The third problem is the deterioration of the patient's quality of life.

Since colorectal cancer patients suffer greatly from colorectal cancer, abdominal pain caused by the auxiliary apparatus for fecal bypass after surgery inflicts severe mental and physical pain on the patient, and some patients require removal of the auxiliary apparatus for fecal bypass due to this pain. In some cases, the patient stopped using the auxiliary apparatus for fecal bypass and put a diaper on. However, this was cumbersome and shameful from the patient's point of view.

The above problems were a long-awaited task to be solved over a period of more than a decade from the year 2000, when the inventor devised the first invention with the Korean registration number 10-0375584, up until now.

The present inventor has contemplated various solutions, and for this solution, he has tried to solve a problem that has persisted for a long time through countless experiments for decades.

Below are some solutions that the present inventor has carried out to solve the problem.

In order to reduce the patient's abdominal pain, the present inventor prescribed Hyoscine-N-Butylbromide, a smooth muscle relaxant analgesic, NSAID, an anti-inflammatory analgesic, and Opioid, an opioid analgesic, to the patient. In this case, the patient's abdominal pain could be relieved. However, due to excessive peristalsis of the intestines, the intestines burst, causing serious complications due to leakage of feces. Therefore, the present inventor also performed reoperation due to this complication. For this reason, the present inventor could not administer sufficient analgesic to relieve the patient's pain.

As such, prescription of analgesic does not solve the problem, so the present inventor tried to solve the problem by injecting a reduced amount of treatment liquid into the patient.

However, in this case, there was a problem that time takes to inject the washing solution was long, which interfered with a daily life of the patient, and even if the amount of the washing solution was reduced, the bowel peristalsis due to the injection of the washing solution was performed, and the abdominal pain of the patient was not reduced.

Furthermore, since small amount of the treatment liquid is injected into the patient, the contents in the intestine could not be mixed with the treatment liquid, and thus could not be discharged to the outside of the intestine due to solidification.

The last solution that the inventor carried out was to open the space of the auxiliary apparatus for fecal bypass. That is, if the patient complains of abdominal pain while injecting the treatment liquid into the patient, stop injecting the treatment liquid and observe. The patient's abdominal pain could go away if the additional injection of the treatment liquid was stopped. If the patient's pain continues even after stopping the injection of the treatment liquid, the problem was solved by opening the space (open the auxiliary apparatus for fecal bypass by decompressing an inner balloon of the auxiliary apparatus for fecal bypass) and discharging the treatment liquid to the outside.

This method was effective in reducing the increased pressure in the intestinal tract by discharging the treatment liquid mixed with feces, which was the cause of a high intestinal pressure, out of the auxiliary apparatus for fecal bypass. As a result, the patient's abdominal pain was reduced or disappeared. In addition, this method has an advantage that there is no risk of intestinal rupture.

However, if this process is repeated during injection of the treatment liquid, the problem may be temporarily solved, but the contents in the intestines are discharged to the outside, which may contaminate the patient and a bed and make the patient uncomfortable.

As a result, although this method is safe, it is time consuming and has a negative impact on the hospital environment by contaminating the surroundings. This process required several manipulations. That is, if the pain continues after locking the injected treatment liquid and waiting for a while, it is necessary to perform an operation to drain the intestinal contents. In most cases, it is difficult for a patient to do it alone, so the help of a caregiver, or nursing personnel is required.

Patients or caregivers, who have to repeat this process several times, become very stressed and regret having chosen a procedure of the auxiliary apparatus for fecal bypass. In severe cases, the patient requested early removal of the auxiliary apparatus for fecal bypass. However, early removal of the auxiliary apparatus for fecal bypass is very dangerous. This is because damage to the anastomosis may occur during the removal process, and preventing leakage of the anastomosis becomes meaningless due to early removal.

This method is time-consuming, cumbersome, and requires the help of other personnel including nursing personnel. Further, ultimately, the quality of life of the patients deteriorated. Moreover, the method causes contamination of patients and beds, which may also endanger the health of other patients by causing contamination of the hospital environment.

As described above, the present inventor has continuously searched for a solution through numerous trials and errors, but most of the solutions seemed to solve the problem, but caused another problem.

However, this trial and error was not just a simple failure. After various trials and errors, the present inventor found that the solution of abdominal pain is fluctuations in intestinal pressure due to peristalsis of the intestines during injection of the treatment liquid, and thus, tried to solve the long-awaited problem in a new way.

DISCLOSURE

Technical Problem

An object of the present invention is to prevent a patient from suffering from abdominal pain, unlike the conventional auxiliary apparatus for fecal bypass, even if the patient uses the present invention.

Another object of the present invention is to provide an auxiliary apparatus for fecal bypass that does not cause damage to the intestinal lining when a patient uses the present invention.

Further another object of the present invention is to provide an auxiliary apparatus for fecal bypass capable of improving a patient's quality of life.

The technical problems to be achieved by the present invention are not limited to the technical problems mentioned above, and other technical problems not mentioned will be clearly understood by those of ordinary skill in the art to which the present invention belongs from the description below.

Technical Solution

The present disclosure relates to an auxiliary apparatus for fecal bypass for bypassing and discharging feces in the intestines.

One embodiment is an auxiliary apparatus for fecal bypass including: a main body part being inserted into an anus and positioned on an inside of intestine; a supporting portion formed to be spaced apart at an interval of 8 mm or more to 25 mm or less along an outer periphery of the main body part and fixing the main body part to be positioned at a rectum by expanding and being in close contact with an inner surface of the intestine when air or liquid is injected thereto; a blocking part installed inside the main body part and expanding when air or liquid is injected so as to close a space inside the main body part; a liquid moving tube installed inside the main body part to prevent closure even if the blocking part is expanded and allowing treatment liquid injected from an outside of an anus to be injected into intestines.

Here, it is preferable that a length of a base of the supporting portion to be set to 4 mm or more to 15 mm or less.

In addition, it is preferable that an outer diameter of the main body part to be set to 10 mm or more to 30 mm or less.

Also, the auxiliary apparatus for fecal bypass of the present disclosure satisfies a formular 1.

The formular 1 is $0<[S-(D+2H)+1.5T]<[5+1.5T]$

Here, what each symbol of the formular 1 represents is as below.

S is an internal diameter of an intestinal tract, H is a height of a supporting portion, D is an outer diameter of a main body part, and T is a thickness of an intestine.

In addition, the auxiliary apparatus for fecal bypass of the present disclosure includes air flow tube having a bypass part communicating with the supporting portion and allowing a plurality of supporting portions to expand at the same time when air is injected.

Here, the liquid moving tube is characterized in being formed to open an upper portion thereof so that the treatment liquid is injected into the intestine, and automatically adjusting pressure inside the intestines by allowing an extra space to which feces mixed with the treatment liquid are partially moved, when pressure of the intestine is increased by a peristalsis of the intestine.

Here, it is preferable that a size of a cross section of the liquid moving tube to be 3 $mm^2$ or more to 23 $mm^2$ or less.

Here, the main body part is positioned inside the auxiliary apparatus for fecal bypass in a form of a long rod set to facilitate an entry of the main body part into an anus, and an upper part thereof includes a cover formed in a round shape and has a symmetrical incision portion with respect to a center.

Here, the auxiliary apparatus for fecal bypass includes, in order for the main body part provided inside the cover to separate from the cover, a pusher in a form of a long rod contacting with a lower portion of the main body part and pushing the main body part upward to move the main body part upward and to make a size of an upper portion of the cover to be greatly deformed so as to allow the main body part entering into an inside of the intestine.

Advantageous Effect

The present invention may reduce pressure in intestines by providing a space through which treatment liquid or mixture may move when an increase and expansion of internal pressure in the intestine occurs due to the peristalsis of the intestine, thereby preventing a patient from abdominal pain.

In addition, since the treatment liquid is automatically supplied into the intestine and refluxed into a liquid moving tube, the treatment liquid is not excessively injected, and abdominal pain is not caused by peristalsis of the intestine, and the treatment liquid may be mixed with the contents in the intestine within a short time, thereby reducing treatment time. As a result, the reduction of abdominal pain and treatment time minimizes a risk of damage to the intestinal wall (erosion) and the auxiliary apparatus for fecal bypass may be removed with minimized pushing of the auxiliary apparatus for fecal bypass inside the intestinal tract.

In addition, the auxiliary apparatus for fecal bypass of the present disclosure is manufactured to have a level that does not damage the intestinal lining while being able to be firmly fixed at a specific position in the intestine, and it does not cause damage to the lining of the intestine of the patient.

Therefore, even if the patient uses the auxiliary apparatus for fecal bypass of the present disclosure, abdominal pain is not induced, and damage to the intestinal lining does not occur, so the quality of life of the patient may be improved.

DESCRIPTION OF DRAWINGS

FIG. 2 shows a cover of the auxiliary apparatus for fecal bypass of the present disclosure.

FIG. 3 shows a pusher of the auxiliary apparatus for fecal bypass of the present disclosure.

FIG. 7*a* shows a state before the auxiliary apparatus for fecal bypass of the present disclosure is drawn into a rectum.

FIG. 8 shows the numerical values of each configuration of the auxiliary apparatus for fecal bypass of the present disclosure.

MODE FOR INVENTION

Figure 1:
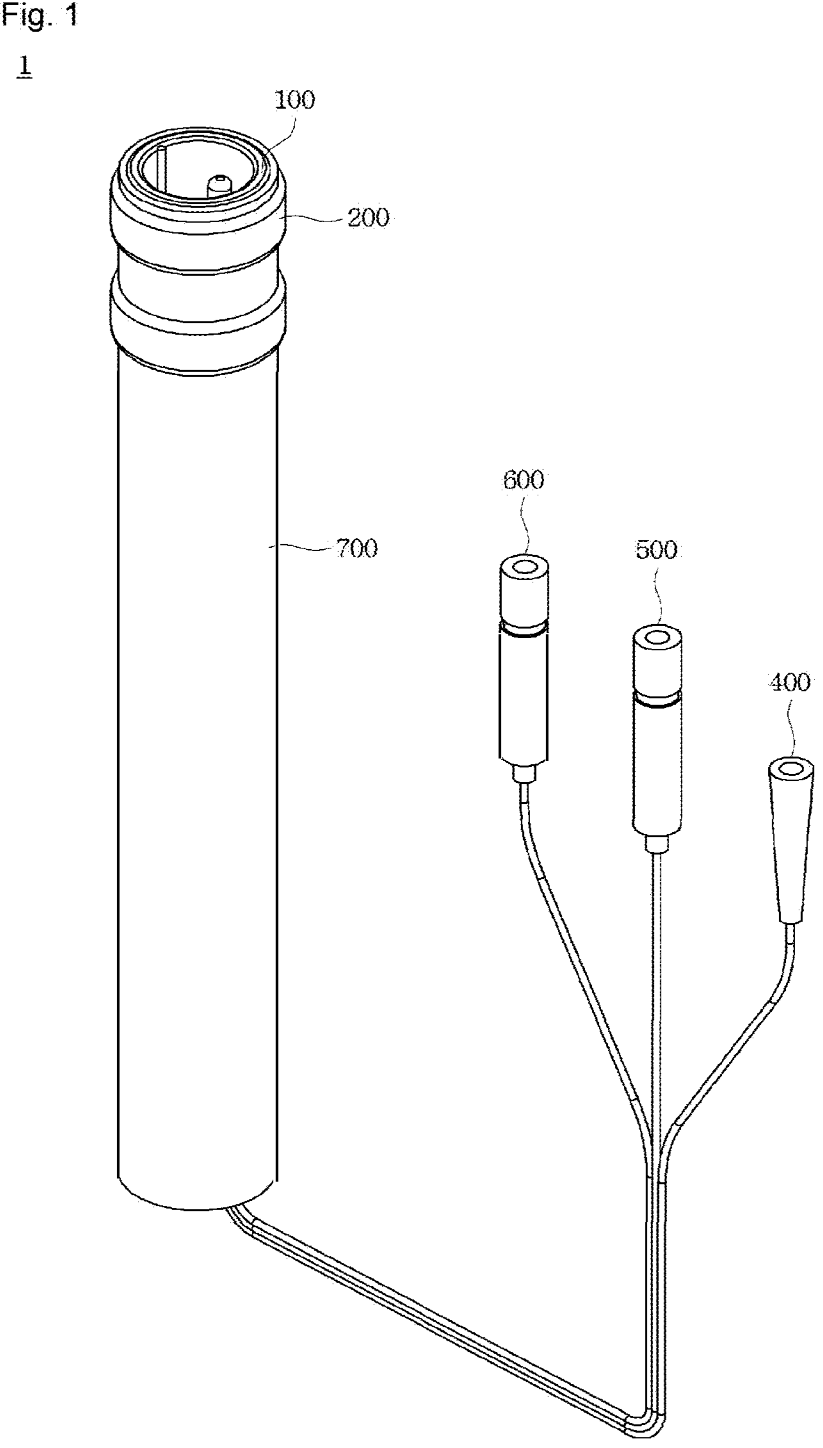
FIG. 1 is a view showing the auxiliary apparatus for fecal bypass of the present disclosure.

Hereinafter, an embodiment of the present disclosure will be described in detail with reference to exemplary drawings. However, this is not intended to limit the scope of the present disclosure.

In assigning reference numerals to the constituent elements in each of the following drawings, the same reference numerals will be used for the same constituent elements even though they are shown in a different drawing. In addition, in the following description, when a detailed description of well-known functions or configurations related to the present disclosure is determined to unnecessarily cloud a gist of the inventive concept, the detailed description thereof will be omitted.

The size, shape or the like of components shown in the drawings may be exaggerated for clarity and convenience of description. In addition, the terms, particularly defined by taking into consideration the configurations and functions of the present invention, are used for description of the present disclosure, and do not limit the scope of the present disclosure.

FIG. 1 is a view showing the auxiliary apparatus for fecal bypass of the present disclosure.

Figure 2:
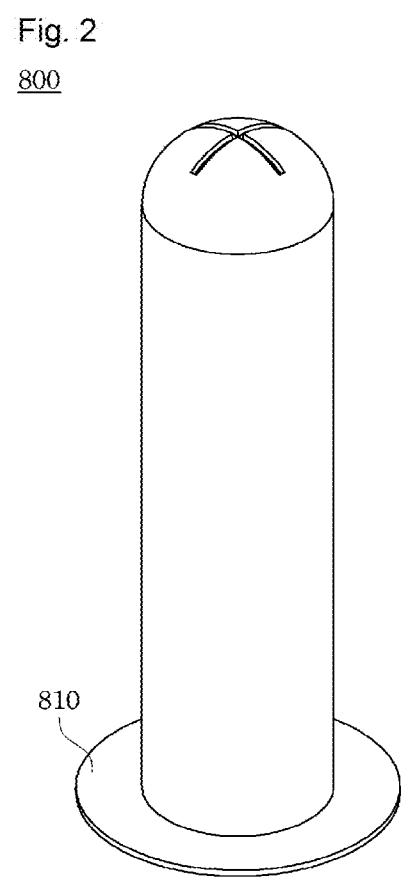

FIG. 2 shows a cover of the auxiliary apparatus for fecal bypass of the present disclosure.

Figure 3:
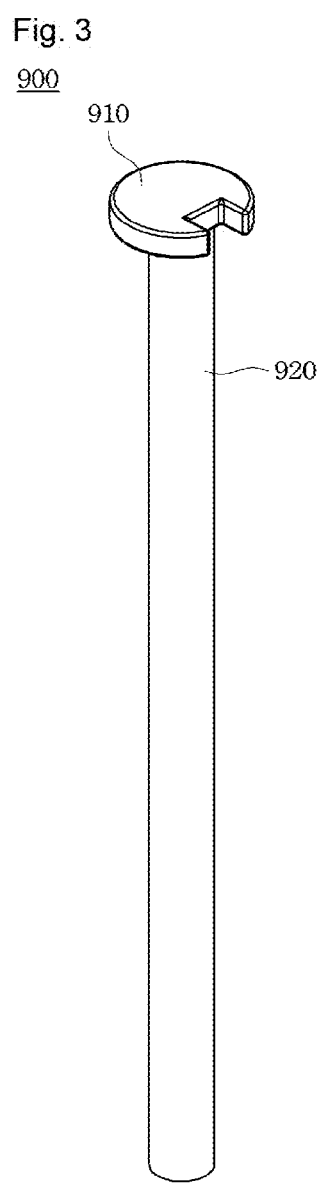

FIG. 3 shows a pusher of the auxiliary apparatus for fecal bypass of the present disclosure.

Figure 4:
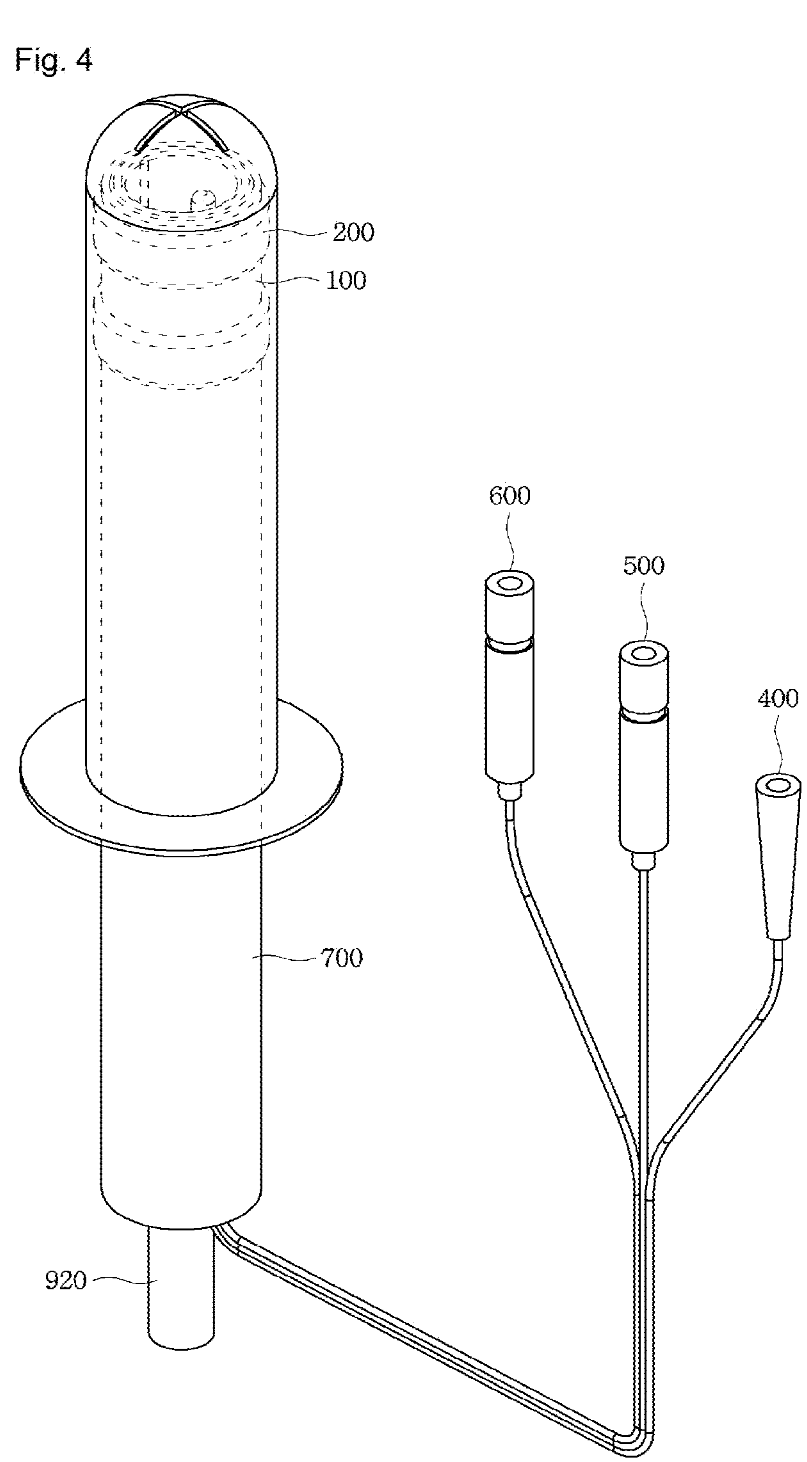
FIG. 4 shows a state in which each configuration of the auxiliary apparatus for fecal bypass of the present disclosure is combined.

FIG. 4 shows a state in which each configuration of the auxiliary apparatus for fecal bypass of the present disclosure is combined.

Figure 5:
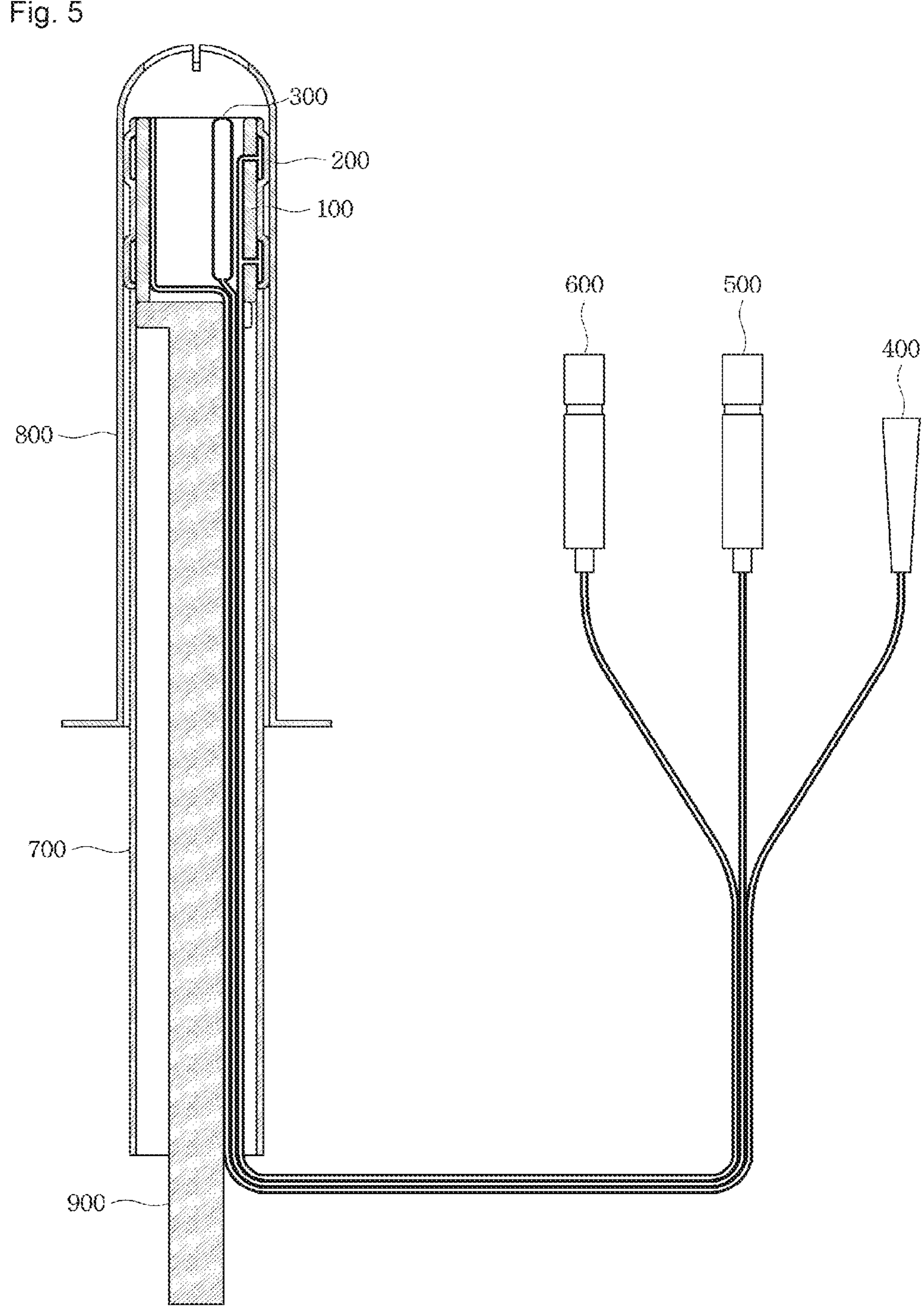
FIG. 5 is a cross-sectional view of a state in which each configuration of the auxiliary apparatus for fecal bypass of the present disclosure is combined.

FIG. 5 is a cross-sectional view of a state in which each configuration of the auxiliary apparatus for fecal bypass of the present disclosure is combined.

Figure 6A:
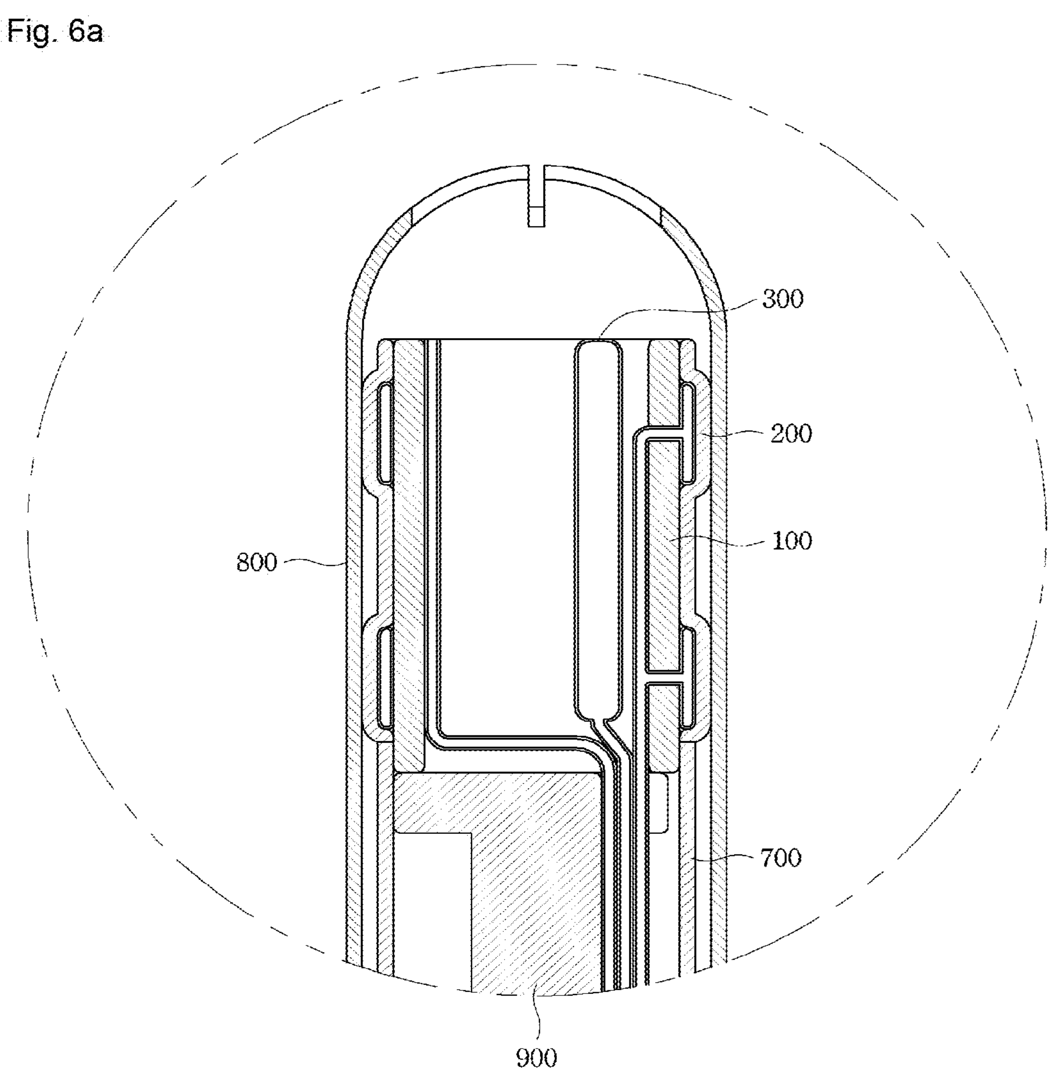
FIG. 6*a* is an enlarged view of only an upper side of FIG. 5.

FIG. 6*a* is an enlarged view of only an upper side of FIG. 5.

Figure 6B:
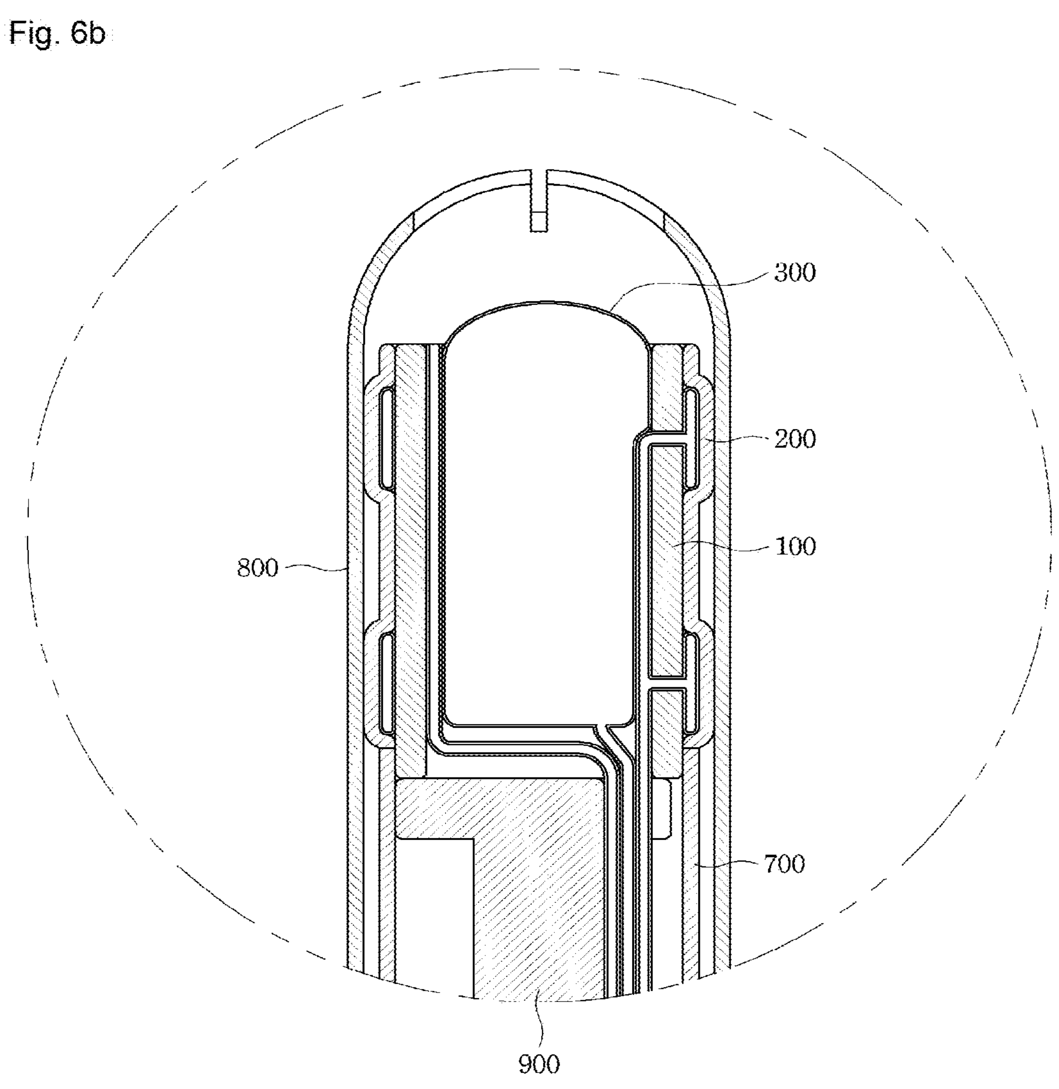
FIG. 6*b* shows a state in which the blocking part is expanded in FIG. 6*a*.

FIG. 6*b* shows a state in which the blocking part is expanded in FIG. 6*a*.

The auxiliary apparatus for fecal bypass of the present disclosure includes a body part 100, a tube 700, a supporting portion 200, a blocking part 300, a liquid moving tube 400, a first air flow tube 500, and a second air flow tube 600.

In addition, the auxiliary apparatus for fecal bypass may further include a cover 800 and a pusher 900.

The body part 100 may be formed in a cylindrical shape. The body part 100 includes a hollow. That is, the upper and lower portions of the body part 100 are opened, and a space is also formed inside the body part 100. To an inner space of the body part 100, a mixture of a treatment liquid and a substance in the intestine to be described later may be discharged.

The tube 700 may be installed on a lower portion of the body part 100. The tube 700 has a perimeter that is slightly larger than a perimeter of the body part 100, thus the body part 100 may be inserted to the tube 700. That is, a lower portion of the body part 100 may be inserted to an upper side of the tube 700. Therefore, it becomes possible to prevent the treatment liquid or a mixture of the treatment liquid and intestinal contents moving through an inner space of the body part 100 from flowing down into a space between the body part 100 and the tube 700.

Although not illustrated, a lower side of the tube 700 may be connected to a pouch in which the treatment liquid or the mixture of the treatment liquid and the intestinal contents may be stored.

A first air flow tube 500 and a second air flow tube 600 may be installed in an inner space of the body part 100. The blocking part 300 may be installed in an inner space of the body part 100, and a supporting portion 200 may be formed on an outer surface of the body part 100 along a circumference of the body part 100.

One of the supporting portions 200 may be formed on an upper circumference of the body part 100, and another of the supporting portions 200 may be formed on a lower circumference of the body part 100 spaced apart therefrom. The blocking part 300 is formed on one side of an inner surface of the body part 100, as seen in FIGS. 6*a* and 6*b*, is connected to the first air flow tube 500, and the two supporting portions 200 may be connected to the second air flow tube 600.

As seen in FIGS. 6*a* and 6*b*, the second air flow tube 600 has a bypass flow path which is connected to each blocking part 300. Therefore, when air is injected into the second air flow tube 600, the supporting portion 200 located on an upper part of the body part 100 and the supporting portion 200 located on a lower part of the body part 100 may be simultaneously expanded. When air is injected into the first air flow tube 500, the blocking part 300 may be expanded.

Here, the first air flow tube 500 and the second air flow tube 600 may be injected with a liquid (saline solution) other than air according to an embodiment.

When the blocking part 300 is expanded, it is possible to close an inner space of the body part 100. Further, when the supporting portion 200 is expanded, the supporting portion 200 may be in close contact with an inner surface of the intestine so that the position of the body part 100 can be fixed. Therefore, a space of the intestines may be divided based on the body part 100. The content thereof will be described later on in detail.

The liquid moving tube 400 may also be installed in an inner space of the body part 100. The liquid moving tube 400 is formed to extend upwards of the body part 100 so as not to be closed even if the blocking part 300 is expanded. Although not illustrated, the liquid moving tube 400 may be connected to a cylinder. Therefore, the treatment liquid supplied by the cylinder may be injected into the intestine.

The cover 800 may be formed in a shape of a long tube, of which an upper portion is formed to be round. In the cover 800, an upper portion and lower portion thereof are open, but the upper portion of the cover 800 may be viewed as if it is closed. In the upper portion of the cover 800, incision lines are formed based on a center. A plurality of incision lines may be formed based on the center of the cover 800.

Accordingly, when a force is applied toward the upper portion of the cover 800 from an inside of the cover 800, the upper portion of the cover 800 may gradually move upward, and a size of the open portion at the center may gradually increase. In addition, a flange portion 810 is formed at a bottom of the cover 800. The flange portion 810 serves to extend a size of a circumference of the cover 800.

The pusher 900 may include a grip unit 920 and a push unit 910. The pusher 900 serves to move the body part 100 by pushing it into the intestine, and it will be described later on.

Figure 7A:
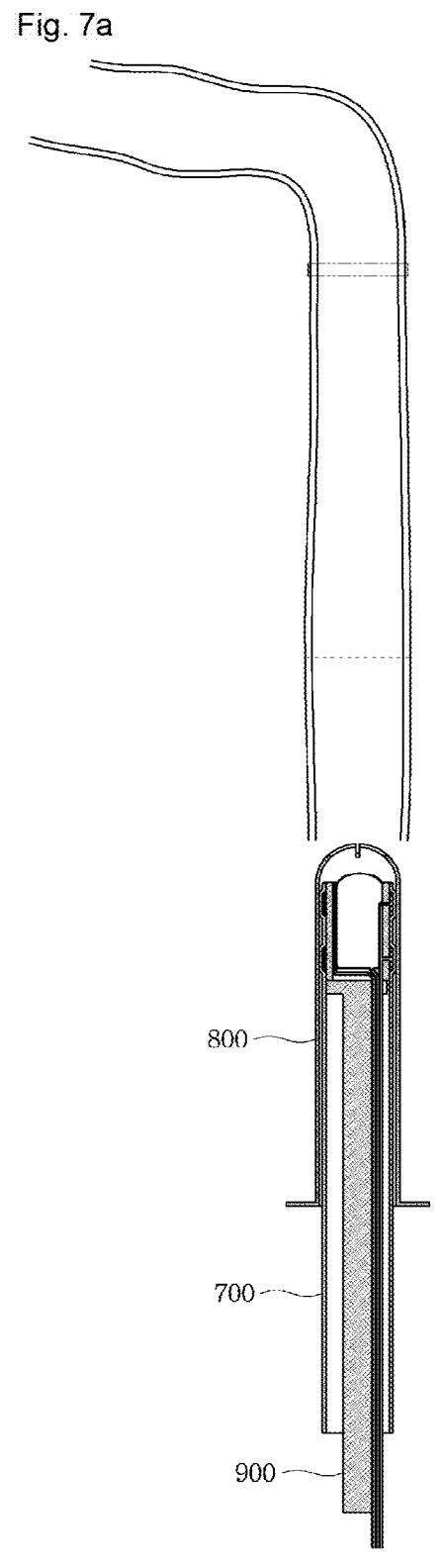

FIG. 7*a* shows a state before the auxiliary apparatus for fecal bypass of the present disclosure is drawn into a rectum.

Figure 7B:
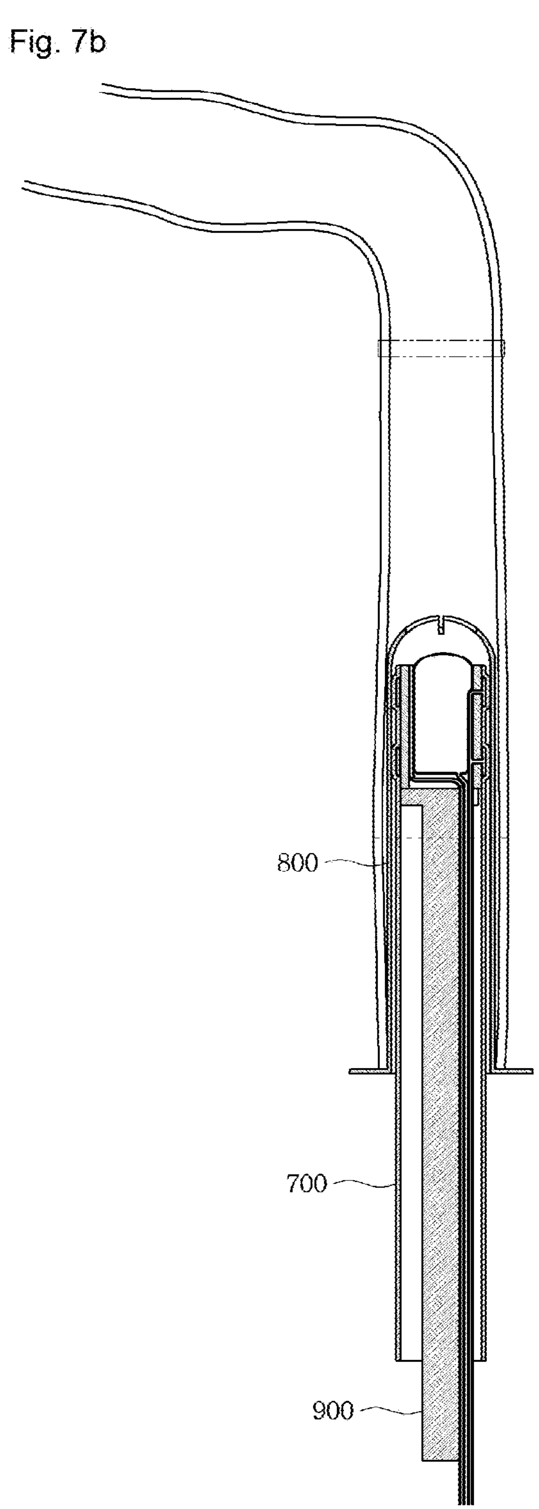
FIG. 7*b* shows a state after the auxiliary apparatus for fecal bypass of the present disclosure is drawn into a rectum.

FIG. 7*b* shows a state after the auxiliary apparatus for fecal bypass of the present disclosure is drawn into a rectum.

Figure 7C:
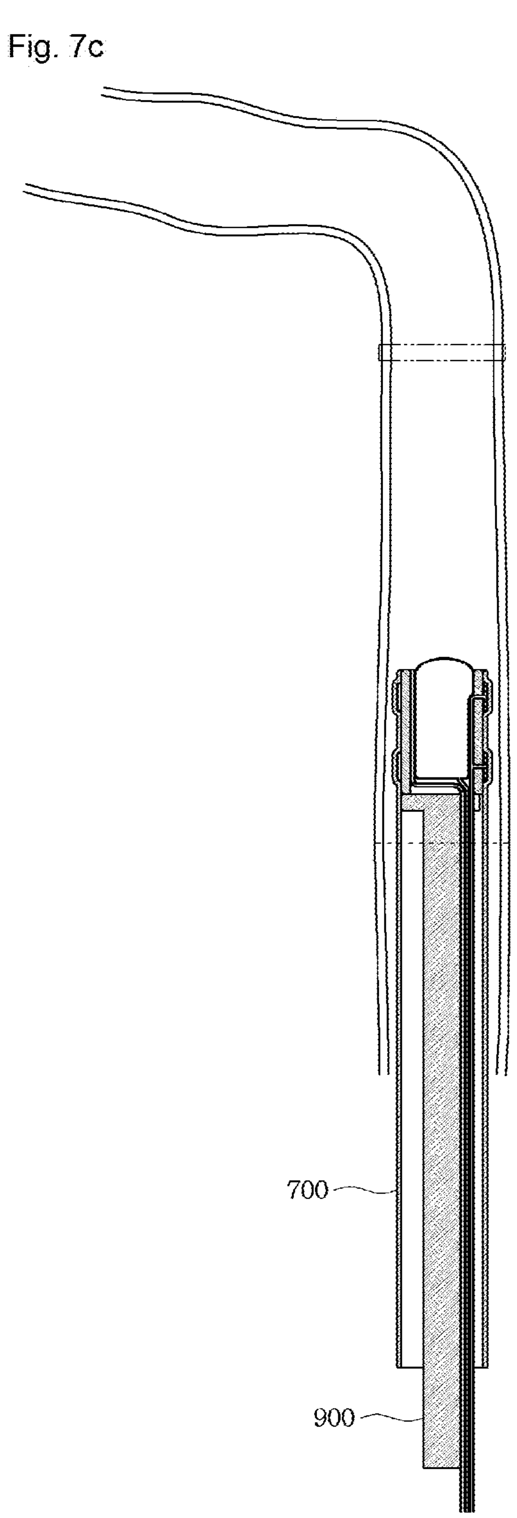
FIG. 7*c* shows a state in which only the cover is removed after the auxiliary apparatus for fecal bypass of the present disclosure is drawn into a rectum.

FIG. 7*c* shows a state in which only the cover is removed after the auxiliary apparatus for fecal bypass of the present disclosure is drawn into a rectum.

Figure 7D:
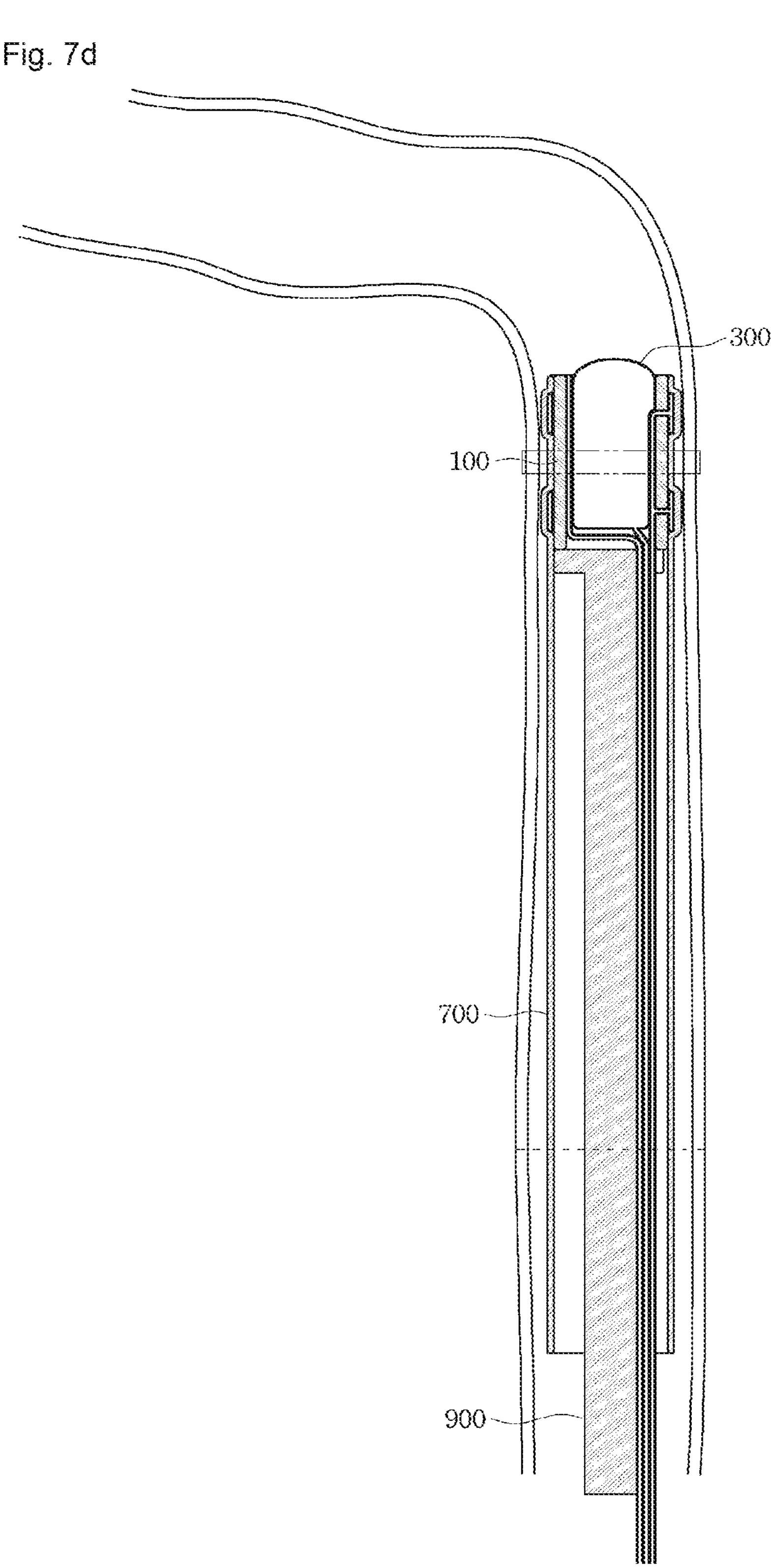
FIG. 7*d* shows a state in which the auxiliary apparatus for fecal bypass of the present disclosure is arranged in a specific position in the intestine by using the pusher.

FIG. 7*d* shows a state in which the auxiliary apparatus for fecal bypass of the present disclosure is arranged in a specific position in the intestine by using the pusher.

Figure 7E:
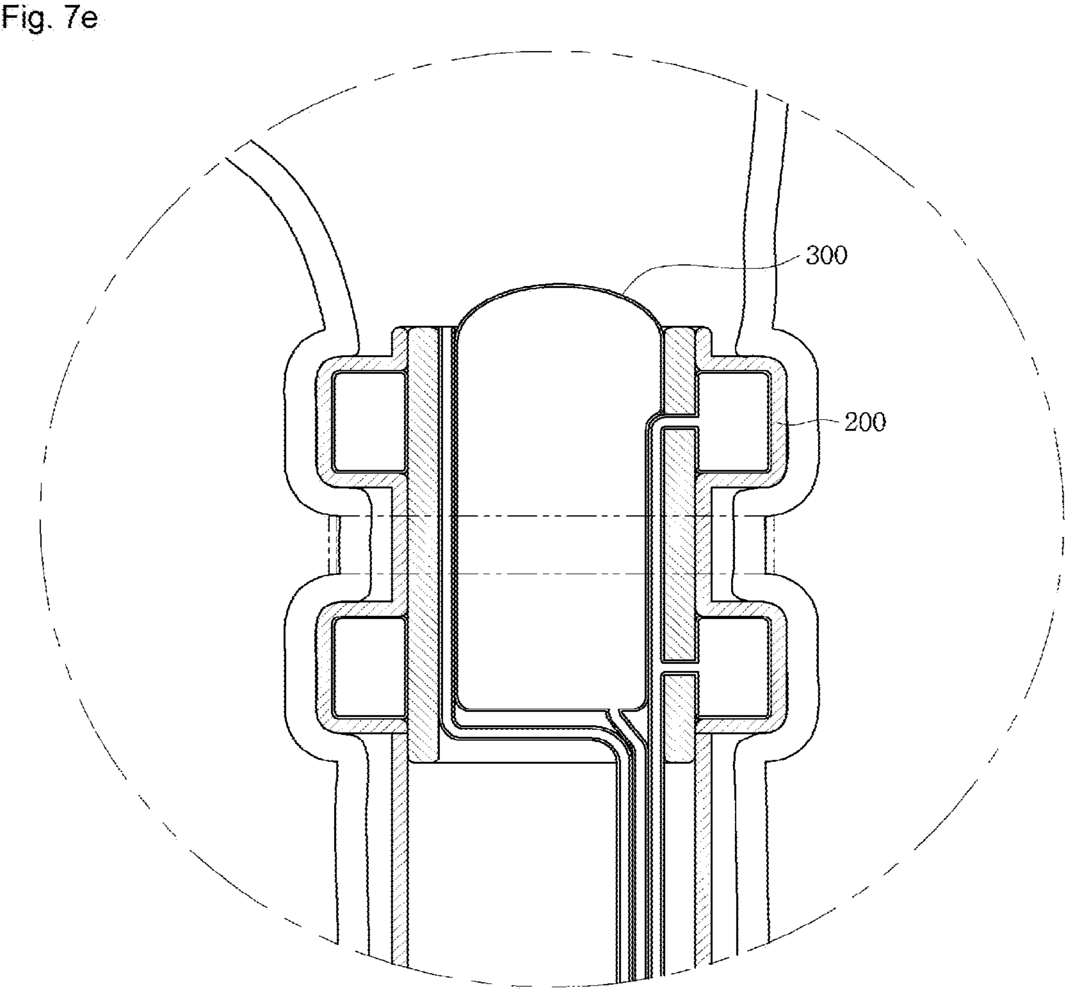
FIG. 7*e* shows a state in which the supporting portion is expanded and the auxiliary apparatus for fecal bypass of the present disclosure is fixed in the intestine.

FIG. 7*e* shows a state in which the supporting portion is expanded and the auxiliary apparatus for fecal bypass of the present disclosure is fixed in the intestine.

Figure 7F:
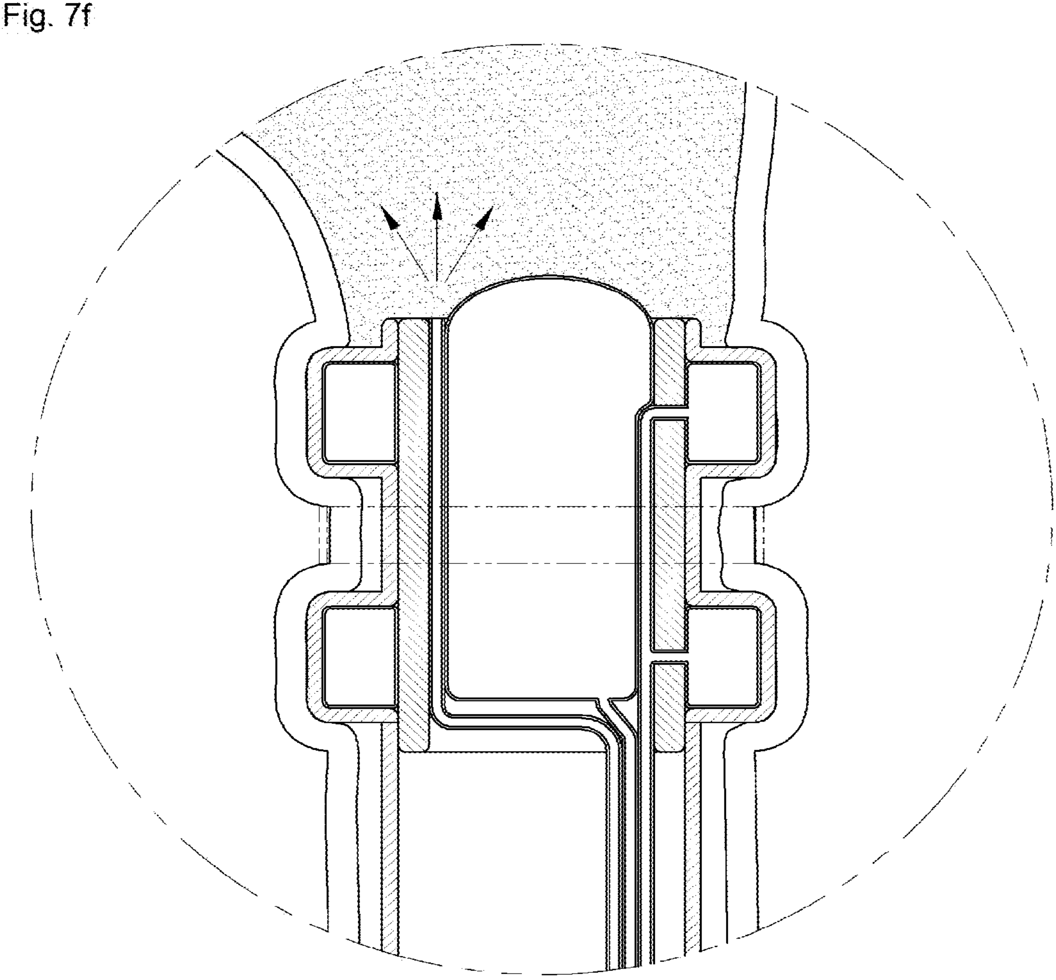
FIG. 7*f* shows a state in which the treatment liquid is supplied into the intestine through the liquid moving tube.

FIG. 7*f* shows a state in which the treatment liquid is supplied into the intestine through the liquid moving tube.

Figure 7G:
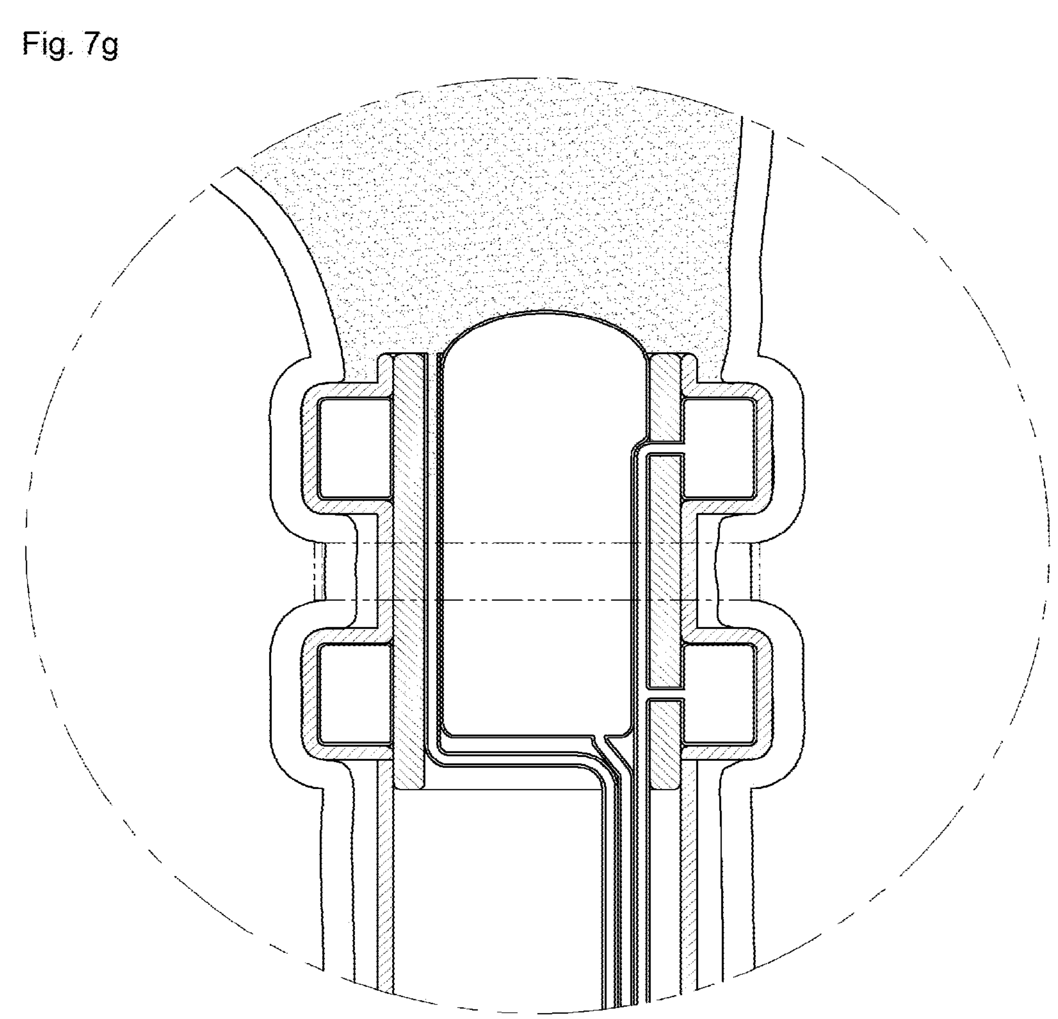
FIG. 7*g* shows a state in which the treatment liquid or a mixture of the treatment liquid and contents in the intestine is refluxed into the liquid moving tube due to an internal pressure of the intestine or the peristalsis of the intestine.

FIG. 7*g* shows a state in which the treatment liquid or a mixture of the treatment liquid and contents in the intestine is refluxed into the liquid moving tube due to an internal pressure of the intestine or the peristalsis of the intestine.

Figure 7H:
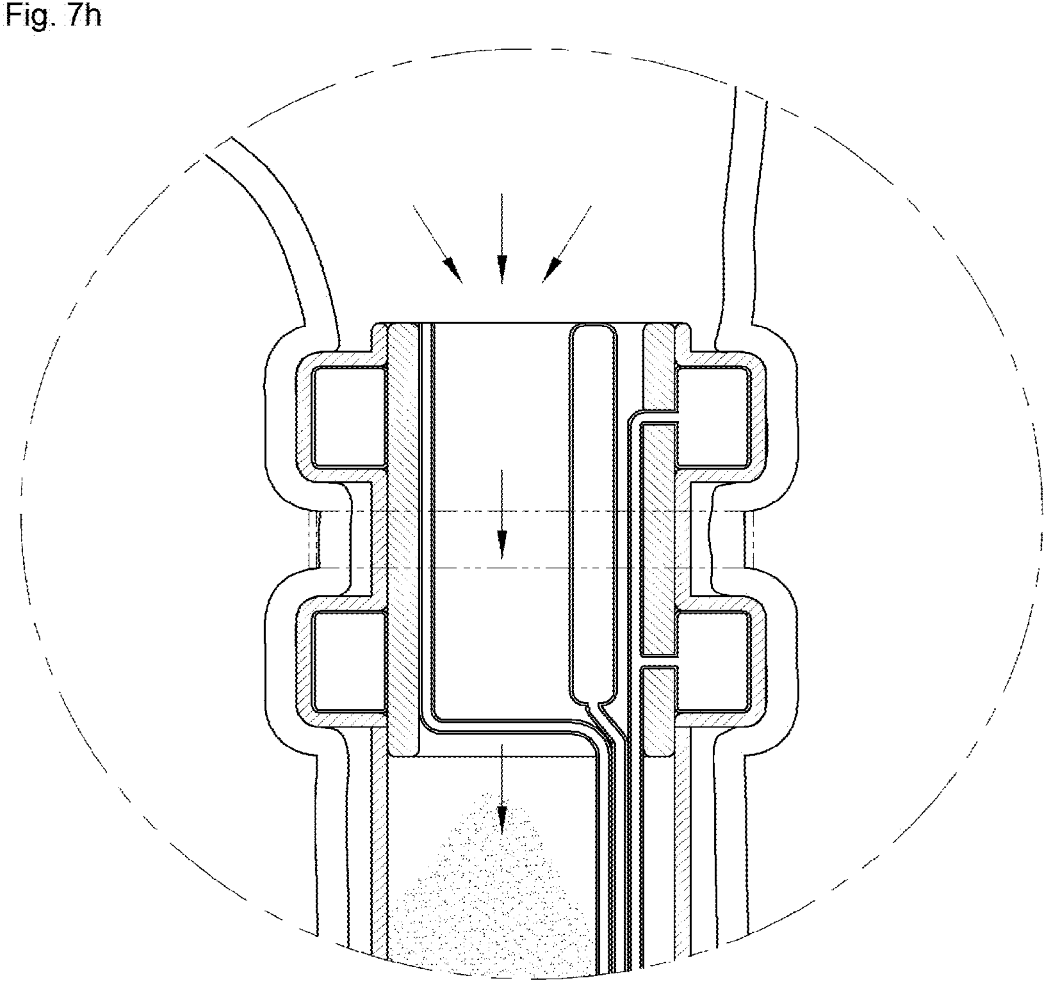
FIG. 7*h* shows a state in which the blocking part shrinks and the treatment liquid or a mixture of the treatment liquid and the contents in the intestine is discharged.

FIG. 7*h* shows a state in which the blocking part shrinks and the treatment liquid or a mixture of the treatment liquid and the contents in the intestine is discharged.

Figure 7I:
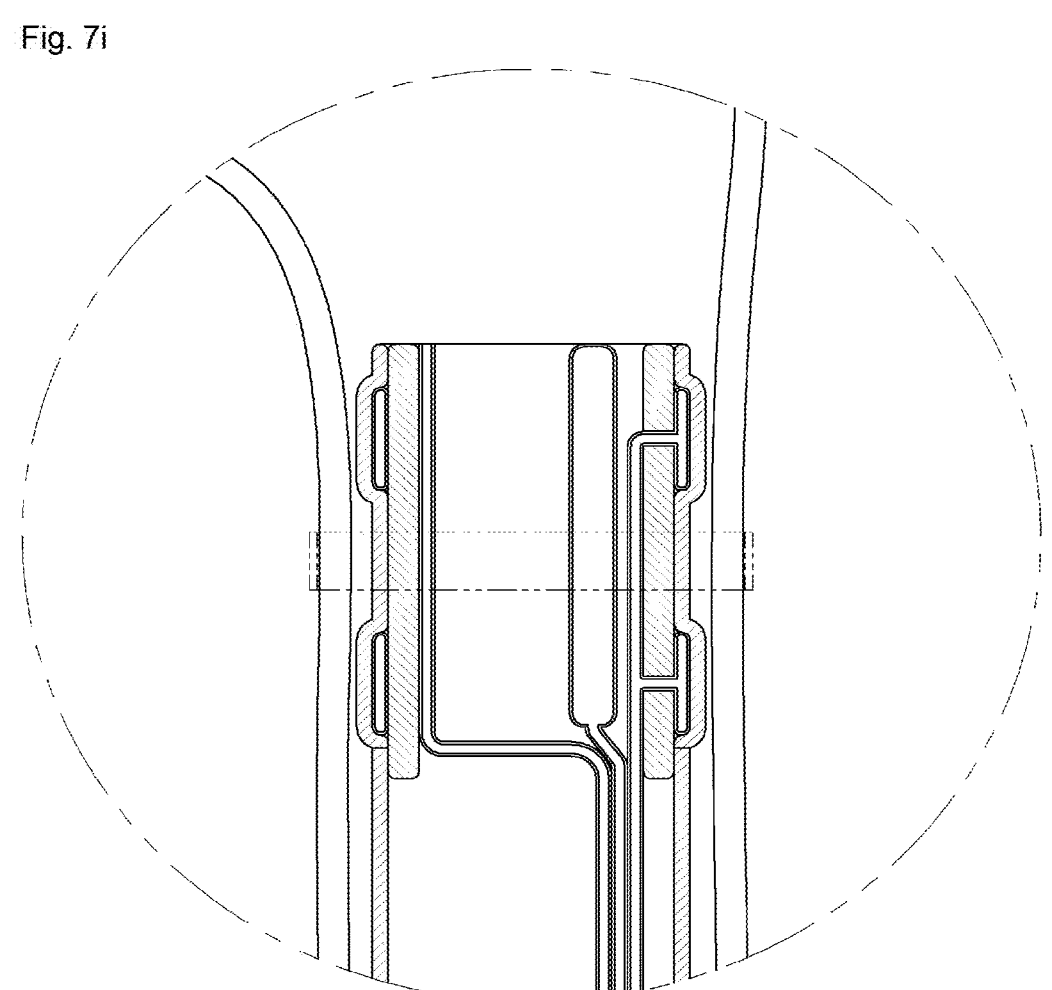
FIG. 7*i* shows a state in which the supporting portion is shrunk.

FIG. 7*i* shows a state in which the supporting portion is shrunk.

Hereinafter, a process where the auxiliary apparatus for fecal bypass of the present disclosure installed in the intestine bypasses and discharges feces will be described.

For a patient, lesion site of the intestine is cut for treatment of colorectal cancer, and then the cut intestine is sutured again, and a biodegradable band is wound around the intestine and fixed at a position spaced upward from the sutured position. Here, the biodegradable band does not pose a problem even if an outer surface of the intestine is tightened by the biodegradable band with a moderate pressure.

For the patient, the body part 100 is placed inside the cover 800. For the patient, air is injected through the first air flow tube 500 and the blocking part 300 is expanded and an inner space of the body part 100 is closed. Further, the push unit 910 of the pusher 900 is disposed to contact a lower portion of the body part 100. Here, since the grip unit 920 of the pusher 900 is formed in a long rod shape, the grip unit 920 may be exposed to the outside.

Gel or lubricant may be applied to the cover 800 and the pusher 900 may be used to be inserted to the patient's anus. When the cover 800 is inserted to the anus of the patient, the flange portion 810 of the cover 800 is not inserted to the anus, and the flange portion 810 contacts the buttocks, thereby supports the cover 800.

When the flange portion 810 is in contact with the buttocks, the cover 800 is withdrawn from the anus. Since the upper portion of the cover 800 has an incision formed with respect to a center as described above, when the cover 800 is withdrawn from the anus, the open portion formed in the center of the cover 800 may become as large as a size equal to a size of the body part 100 and a size of the supporting portion 200 combined, and only the cover 800 may be withdrawn from the anus.

The doctor grabs the grip unit of the pusher 900 and pushes it further into the patient's anus so that the body part 100 passes the suture part of the intestine and is positioned at a part where the band is bound. Here, regarding the position of the body part 100, it is preferable that the supporting portion 200 positioned on the upper part of the body part 100 and the supporting portion 200 positioned on the lower part of the body part 100 to be located symmetrically with respect to the band.

Thereafter, for the patient, air or liquid is injected into the supporting portion 200 through the second air flow tube 600 so as to expand the supporting portion 200. The expanded supporting portion 200 is in close contact with an inner surface of the intestine. Here, since the band presses the intestines with a set pressure, the supporting portion 200 may push the intestines slightly.

As such, when the supporting portion 200 is expanded, the patient's intestines may be divided into upper and lower portions with respect to the body part 100. That is, the space of the intestines may be closed due to the blocking part 300, the body part 100, and the supporting portion 200.

When the supporting portion 200 is expanded, the treatment liquid may be injected into the liquid moving tube 400 by manipulating the cylinder, for the patient. The doctor may inject 600 to 1000 cc of the treatment liquid for 20 to 25 minutes. The intestines injected with the treatment liquid undergo peristalsis and the treatment liquid is mixed with the contents of the intestines.

After that, air or liquid is withdrawn from the blocking part 300 using the first air flow tube 500 so as to make the blocking part 300 shrink again. Then, in the intestines that were closed, a moving space is formed in the inner space of the body part 100, and the mixture in which the treatment liquid and the contents of the intestine are mixed is discharged to the outside through the tube 700.

For the patient, using the second air flow tube 600, the supporting portion 200 becomes shrunk, and it is possible to finish the treatment by pulling the tube 700 and moving the body part 100 out of the intestine.

Although the above treatment process enables the bypass discharge of feces, there are problems occurred, which are abdominal pain of the patient due to an increase in intestinal pressure generated when the treatment liquid is injected, and a damage in intestinal lining due to compressed fixation of the supporting portion 200 because of the peristalsis of the intestine when the supporting portion 200 is closely fixed to an inner surface of the intestine.

Therefore, it is necessary to solve the above problems.

However, when solving the above problems, the original role of the configuration of the auxiliary apparatus for fecal bypass should be maintained. That is, the blocking portion 300 should close the inner space of the body part 100 during expansion, and the supporting portion 200 should be in close contact with the intestinal tract during expansion.

In order to solve the above problems, the numerical values of each configuration were changed under various conditions. All of the following numerical changes are result of performing a cycle, for several times, where the supporting portion 200 is expanded, the treatment liquid is injected into the intestine, the internal pressure of the intestine is increased after sufficient time has elapsed, the intestines go through sufficient peristalsis, and whether there is damage to intestinal lining or not is checked.

Figure 8:
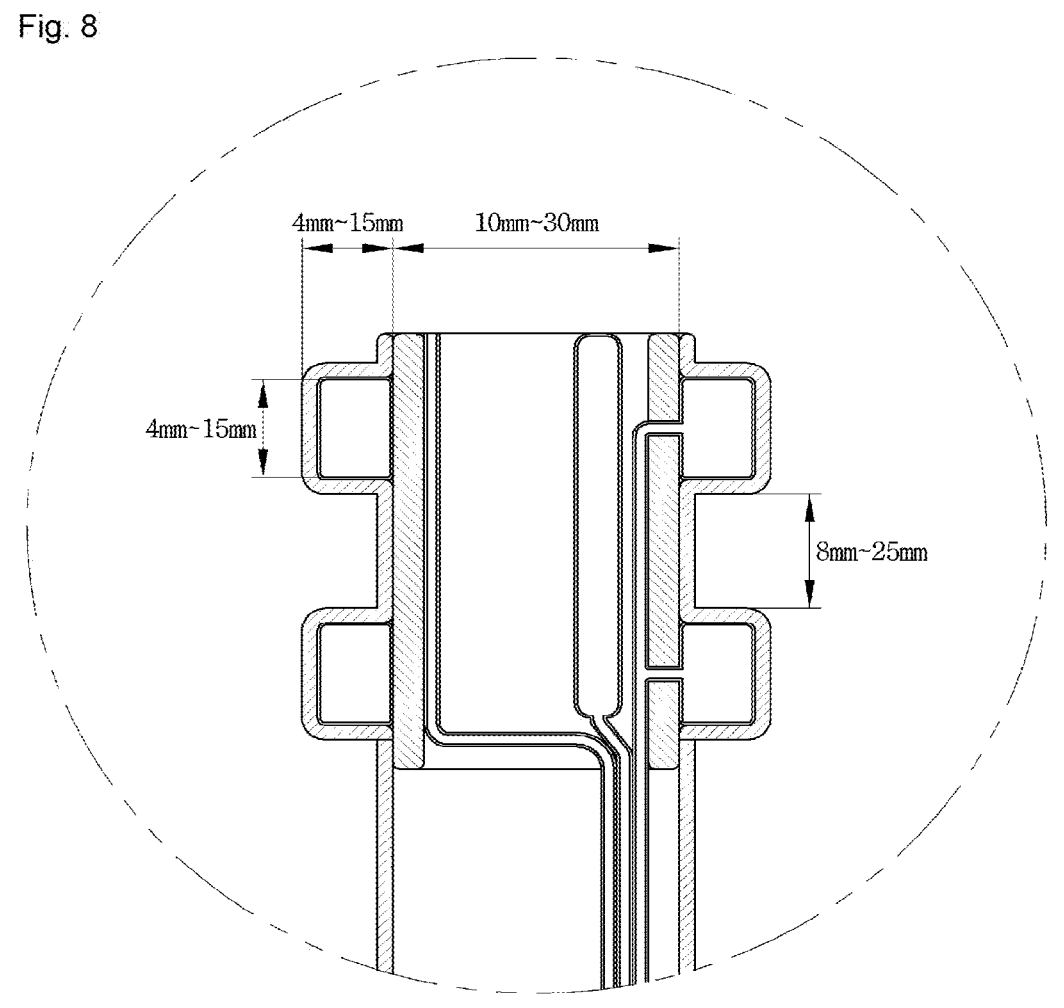

FIG. 8 shows the numerical values of each configuration of the auxiliary apparatus for fecal bypass according to the present disclosure.

*The diameter and thickness of the intestines vary depending on a person and a type of disease. The intestine is composed of a special soft and elastic tissue, and a diameter and thickness vary during expansion and contraction.

Therefore, it is difficult to accurately measure a diameter and thickness. Therefore, it is difficult to insert a solid instrument into the intestine and to have a function to stop a flow of the contents in the intestine. Moreover, there should be no damage to the intestinal tract during these functions. This is because the intestinal tract is very sensitive to pressure, and it is very difficult to secure the intestines safe when fixing solid instruments to the intestines from the outside. However, the present invention overcomes these difficulties.

In order to devise the present invention, it is primarily important to set the outer diameter of the body part 100. If the outer diameter of the body part 100 is large, it is convenient to inject the washing solution, but if it is set incorrectly, rupture of the patient's intestines may occur.

If the diameter of the intestine is large, a sum of the outer diameter of the body part 100 and a height of the supporting portion 200 is not greatly affected, but if the diameter of the intestine is small, the sum is greatly affected, therefore, measurement of the diameter of the intestines has been performed for various patients and based on this measurement, the acceptance range of the intestine was checked, and the obtained value was 18 to 60 mm.

That is, the auxiliary apparatus for fecal bypass can be fixed to a small intestine only when a size of the overall cross-section is 18 to 60 mm when the supporting portion 200 is expanded, thereby the rupture of the intestine may be prevented. The auxiliary apparatus for fecal bypass of the present disclosure must be manufactured within the size of this set cross-section, and the outer diameter of the body part should be 10 mm at minimum to 30 mm at maximum in consideration of the injection of washing solution, ease of manufacture, and obstruction of mucous membrane damage.

Of course, larger variations may exist depending on the patient's condition, but the above range will be sufficient by standardizing data obtained from a large number of patients.

First, the outer diameter of the body part 100 was set in units of 10 mm.

The reason why the outer diameter of the body part 100 was set in units of 10 mm was that when it was smaller than 10 mm, a problem where the treatment liquid diluted with feces was not properly discharged was found, and the starting point was set to 10 mm.

Another reason for setting the starting point of the outer diameter of the body part 100 to 10 mm is derived from the results of various clinical experiments performed by the present inventor. Rectal tubes commonly used in clinical trials have an outer diameter of 10 mm or less.

However, in the rectal tube used in clinical trials, a problem of clogging a passage by the treatment liquid diluted with feces was continuously observed. The present inventor has continuously recognized these problems in clinical trials. Therefore, the present inventor recognized that the outer diameter of the body part 100 should be at least 10 mm when designing the present invention. In addition, based on this idea, various instruments with different outer diameters were manufactured and tested on animals. As a result, it was found that the outer diameter of the body part 100 should be greater than 10 mm.

Therefore, in the present disclosure, the starting point of the outer diameter of the body part 100 was set to 10 mm.

Further, the final point of the outer diameter of the body portion 100 was set to 30 mm.

The reason is that if the outer diameter of the body part 100 is greater than 30 mm, the size becomes too large, so that it gets difficult to insert the apparatus to the intestine through the anus. Also, because use of too large size may damage the anastomosis made with a circular stapler normally used for intestinal anastomosis. For reference, an outer diameter of the circular stapler is about 25 to 34 mm.

Therefore, in order to avoid damage to the anastomosis while considering the acceptance range of the intestine when removing the auxiliary apparatus for fecal bypass of the present disclosure, it is preferable that the size of the outer diameter of the body part 100 is 30 mm or less. If the size of the body portion 100 exceeds 30 mm, this is because it becomes a problem when inserting or removing it into the intestinal tract. Therefore, the size of the outer diameter of the body portion 100 is preferably 30 mm or less at maximum.

In the end, it was concluded that the body part 100 of which the outer diameter set to 10 mm to 30 mm can be safely and effectively used depending on the thickness of the intestinal tract. In this way, the present inventor set the outer diameter of the body part 100, and then proceeded with the experiment on intestinal mucosa damage according to a height change of the supporting portion 200.

The present inventor used a physiological saline solution when changing the height of the supporting portion 200.

In addition, whether the intestines were damaged due to a change in the height of the supporting portion 200 was confirmed through an animal experiment. For animal experiments, hybrid dogs weighing 15 kg to 26 kg or less were used. This is because the intestines of a crossbreed dog of this size are similar to the size of a human intestine.

(1) Whether the intestinal mucosa is damaged according to the height change of the supporting portion 200 when the outer diameter of the body part 100 is 10 mm The height of the supporting portion 200 to be described below refers to a sum of the heights of the supporting portion 200 installed at a position where the supporting portion 200 is symmetrical to the outside of the body part 100. For example, if the height of the supporting portion 200 is 9 mm when expanded, the two supporting portions 200 expand at symmetrical positions, and thus the height of the supporting portion 200 is 18 mm.

Animal experiments were conducted on the large intestine of hybrid dogs weighing 15 to 19 kg. The samples obtained through these crossbreeds were sufficient for generalization.

TABLE 1

| | Height of the supporting portion(mm) | | | | | | | | | | |
|---|---|---|---|---|---|---|---|---|---|---|---|
| | 1 | 3 | 5 | 7 | 9 | 11 | 13 | 15 | 17 | 18 | 19 |
| Damage to the inner side walls of the intestines | X | X | X | X | X | X | X | X | X | X | ○ |

As a result of checking whether the inner wall of the intestinal tract is damaged (mucosal damage, rupture of the serous membrane, etc.), by gradually increasing the height of the supporting portion 200 from 1 mm when the outer diameter of the body part 100 is 10 mm, the inner wall was not damaged until the height of the supporting portion 200 reached 18 mm (the height of one supporting portion 200 was 9 mm, the sum of the outer diameter of the body part 100 and the height of the supporting portion 200 was 28 mm). However, damage (mucosal damage, rupture) of the mucous membrane of the hybrid dogs began to appear when the height of the supporting portion 200 reached 19 mm or more. However, when the height of the supporting portion 200 is less than 8 mm, a problem in which the auxiliary apparatus for fecal bypass is moved was observed since the supporting portion 200 could not closely contact with the inner wall of the intestine, and the intestinal pressure increased. However, when the height of the supporting portion 200 was set to 8 mm or more, this problem has been solved.

(2) Whether the intestinal mucosa is damaged according to the height change of the supporting portion 200 when the outer diameter of the body part 100 is 20 mm When the outer diameter of the body part 100 was 20 mm, the experiment was targeted for the large intestine of hybrid dogs weighing 19 kg or more to 22 kg or less.

TABLE 2

| | Height of the supporting portion(mm) | | | | | | | | | | |
|---|---|---|---|---|---|---|---|---|---|---|---|
| | 1 | 3 | 5 | 7 | 9 | 11 | 13 | 15 | 17 | 19 | 21 |
| Damage to the inner side walls of the intestines | X | X | X | X | X | X | X | X | X | ○ | ○ |

As a result of the experiment, the rupture of the intestinal mucosa was observed from when the height of the supporting portion 200 was 19 mm or more (the height of the supporting portion 200 was 9.8 mm, the size of the outer diameter including the body part 100 was 39 mm or more).

(3) Whether the intestinal mucosa is damaged according to the height change of the supporting portion 200 when the outer diameter of the body part 100 is 30 mm When the outer diameter of the body part 100 was 30 mm, the experiment was targeted for the large intestine of a hybrid dog weighing 23 kg or more to 26 kg or less.

TABLE 3

| | Height of the supporting portion(mm) | | | | | | | | | | |
|---|---|---|---|---|---|---|---|---|---|---|---|
| | 1 | 3 | 5 | 7 | 9 | 11 | 13 | 15 | 17 | 18 | 19 |
| Damage to the inner side walls of the intestines | X | X | X | X | X | X | X | X | X | X | ○ |

As a result of the experiment, when the height of the supporting portion 200 exceeded 18 mm (the height of the supporting portion 200 was 9 mm, the size of the outer diameter including the body part 100 was 48 mm or more), rupture of the intestinal mucosa was observed.

(4) As a result of the review, when the outer diameter of the body part 100 is 10 mm or more to 30 mm or less, if the height of the supporting portion 200 is 8 mm or more to 18 mm or less, damage to the intestinal lining may be avoided due to the change of the numerical value depending on the diameter of the intestinal tract.

Overall, it is preferable that the height of the supporting portion 200 is 8 mm to 18 mm. The reason is that when the height of the supporting portion 200 is less than 8 mm, when closing the blocking part 300 and injecting the washing solution into the intestine, a problem occurs that the supporting portion 200 is not properly fixed, and when the height of the supporting portion 200 exceeds 18 mm, damage to the intestinal mucosa or the outer wall of the intestine is caused.

On the other hand, since the biodegradable band is tightened around the intestine as described above, damage to the mucous membrane of the intestine occurs depending on the spacing of the supporting portion 200. Therefore, it is important that the spacing between the supporting portion 200 positioned on the upper part and the supporting portion 200 positioned on the lower part of the body part 100 to be set appropriately.

TABLE 4

| | Spacing between the supporting portions 200(mm) | | | | | |
|---|---|---|---|---|---|---|
| | 4 | 5 | 6 | 7 | 8 | 9 |
| Damage to the inner side walls of the intestines | ○ | ○ | ○ | ○ | X | X |

As a result of performing the experiment, from when the spacing between the supporting portions 200 is 8 mm or more, it was confirmed that the intestinal mucosa was not damaged by the band, as the spacing between the supporting portion 200 positioned on the upper part and the supporting portion 200 positioned on the lower part of the body part 100 is sufficiently widened, with respect to the band. Therefore, it is preferable that the supporting portion 200 to be installed at the spacing of 8 mm from the body part 100. In addition, it will be preferable that the spacing between the supporting portions 200 to be limited to a maximum of 25 mm or less.

When the spacing between the supporting portions 200 is 25 mm or more, the length of the body part 100 becomes too long, making it difficult to follow the curve of the rectal region or the intestinal tract region of the anastomosis site in the pelvis.

Since the thickness of the intestinal tract itself is at least 1 to 1.5 mm, the spacing between the two supporting portions 200 should be 4 mm or more so that even a narrow string to fix the apparatus inside the intestinal tract can be tied. If the intestinal tract is not normal (if intestinal edema or fibrosis thickened the intestinal tract), further spacing is required. However, it is apparent that no damage is done to the intestinal tract as well as that the tying a string is available.

As a result of an experiment using a prototype apparatus with various spacings between the supporting portions 200, mucosal damage appeared from the first day after surgery prior to widening the spacing between the supporting portions 200 to 8 mm or more.

However, when the spacing between the supporting portions 800 is 8 mm or more, although mucosal damage was often observed, peritonitis did not occur due to the mucosal damage. That is, the mucosal damage was within the acceptable range.

Therefore, it is preferable to set the spacing between the supporting portion 200 positioned on the upper part of the body part 100 and the supporting portion 200 positioned on the lower part thereof to be 8 mm or more to 25 mm or less, and set the size of the base of the supporting portions 200.

In addition, when the spacing between the supporting portion 200 positioned on the upper part of the body part 100 and the support part 200 positioned on the lower part thereof is less than 8 mm, it was easy to remove the auxiliary apparatus for fecal bypass of the present disclosure, but in a state where the blocking part 300 is closed, when pressure by the peristalsis is received, the auxiliary apparatus for fecal bypass may be twisted by the pressure in a peristalsis direction, by a slight shaking existing in the body part 100.

Due to this, the longitudinal axis of the body part 100 is displaced from the longitudinal axis of the intestinal tract, and the flow of intestinal contents is disturbed when the blocking part 300 is opened. In severe cases, the distortion progresses, and the body part 100 completely blocks the intestinal tract, resulting in a problem that the treatment liquid and the mixture is not be discharged.

If the distance between the supporting portion 200 positioned in the upper part of the body part 100 and the supporting portion 200 positioned in the lower part thereof is more than 25 mm, it is difficult to remove the auxiliary apparatus for fecal bypass after the treatment is completed, and therefore, when the auxiliary apparatus for fecal bypass was removed, a problem was found that a damage occurred to the mucous membrane in the intestine.

In addition, when removing the auxiliary apparatus for fecal bypass, since the intestinal tract through which the auxiliary apparatus for fecal bypass passes is curved along the structure of the sacrum, it was difficult to remove the auxiliary apparatus for fecal bypass, in case a hard portion of feces was too long. When the spacing between the supporting portion 200 positioned in the upper part of the body part 100 and the supporting portion 200 positioned in the lower part thereof is more than 25 mm, it was difficult to remove the auxiliary apparatus for fecal bypass.

TABLE 5

| | Diameter of the supporting portion 200(mm) | | | | | | |
|---|---|---|---|---|---|---|---|
| | 1 | 2 | 3 | 4 | 5 | 6 | 7 |
| whether fixed and closed or not | X | X | X | ○ | ○ | ○ | ○ |

As described above, it is important not to damage the intestinal mucosa, but it is also important that the auxiliary apparatus for fecal bypass is stably fixed in the intestine despite the pressure peristalsis within the intestine. Otherwise, the auxiliary apparatus for fecal bypass may not serve its own function as an auxiliary apparatus for fecal bypass, and the feces flow into the anastomosis site and leakage occurs. Therefore, in the above experiment, the size of the base of the supporting portion 200 is made to be different by changing the length of the base, when the minimum height of the supporting portion 200 that does not damage the mucous membrane in the intestine is 8 mm. As a result of the experiment, if the diameter of the base of the supporting portion 200 was less than 8 mm, the auxiliary apparatus for fecal bypass was moved by the peristalsis of the intestine or the internal pressure of the intestine, or could not partition the intestine, and the treatment liquid or mixture flowed into the anastomosis site and leakage was observed. The smaller the size of the base of the supporting portion 200, the better, but if the size is too small, it is difficult to manufacture a product. Therefore, it is ideal that the base of the supporting portion 200 to be the minimum and have the maximum height. Because, if the size of the base of the supporting portion 200 is large, the overall length of the body part 100 increases in proportion to this, which is not ideal.

If a length of the body part 100 is too long, it is difficult to pass through a pelvic curve of the rectum. The pelvic curve is a curved region formed by the sacrum and coccyx. The rectum is closely attached to the sacrum, so the sacrum and rectum usually have the same curve. Therefore, when the auxiliary apparatus for fecal bypass passes through the rectal region, if the length of the body part is long, passage obstruction occurs. The reason that passage obstruction should be considered is that it may cause organ damage. The conclusion drawn from this is that the shorter the length of the body part, the better.

However, this cannot be realized. Because when the length of the body part is too short, there is a problem in maintaining the same axis (longitudinal axis) as the intestine therewithin. When the auxiliary apparatus for fecal bypass is in the intestine, it may be subjected to asymmetric pressure depending on the quality of the contents (the contents of the large intestine may exist in both solid and liquid gas and do not always come down with symmetry), and the longitudinal axis of the body part may deviate from the longitudinal axis of the intestinal tract.

As a result, displacement of the auxiliary apparatus for fecal bypass (displacement from the band area) or obstruction of the bowel (occlusion) may occur. Therefore, the length of the body part should be at least longer than the diameter of the intestinal tract.

On the other hand, increasing the height of the supporting portion 200 is the same as increasing the outer diameter of the body part, so if the height of the supporting portion 200 is higher than the predetermined height, the intestines are overexpanded, which may cause tearing of serosa of the intestine.

Therefore, the lower the height of the supporting portion 200, the safer the intestinal tract. However, if it is too low, the body part 100 may not be sufficiently supported, and the body part 100 may be easily separated from the band site. Therefore, the minimum height that does not displace the apparatus and the maximum height that does not tear the serosa of the intestine should be determined.

This height was 8 mm, as seen from the table in which the above-mentioned height of the supporting portion was tested. Below this height, displacement of the apparatus could occur. Since the maximum height may vary depending on the outer diameter of the body part, it is safe if the height of the supporting portion 200 is 18 mm or less when using an apparatus having an outer diameter sized 30 mm of the body part 100 in a clinical trial.

Also, there is a problem in the manufacturing context. If the base of the supporting portion 200 is large, the height of the supporting portion may be increased stably, but there is a limit if the size of the base is small. When the size of the base of the supporting portion 200 is small, even if the height of the supporting portion 200 is high, sufficient bearing capacity was not provided. When the height of the supporting portion 200 is high and the size of the base of the supporting portion 200 is small, sufficient bearing capacity was not provided, as the body part is being pushed when the force is given.

As a result of this experiment, the size of the base of the supporting portion 200 should be 4 mm or more to enable to play the role of the supporting portion 200. When making the size of the base of the supporting portion 200 larger, it became possible to form the supporting portion 200 with excellent bearing capacity, but if the base of the supporting portion 200 is too large, the length of the entire body part becomes longer accordingly, thus it was preferable to form the size of the base to 15 mm or less.

In summary, when the auxiliary apparatus for fecal bypass of the present disclosure is formed to satisfy the following conditions,

*

Outer diameter of body part: 10 mm or more to 30 mm or less (ii) height of the supporting portion: 8 mm or more to 18 mm or less (iii) spacing between the two support parts 200: 8 mm or more to 25 mm or less (iv) size of the base of the supporting portion: 4 mm or more to 15 mm or less (v) length of body part: 25 mm to 55 mm it becomes possible to minimize damage to the inner wall of the intestine while performing the original role of the auxiliary apparatus for fecal bypass.

In order to find the optimal value of the auxiliary apparatus for fecal bypass having the above numerical limitations, it is inevitable to select the optimal value in relation to a body. Since each person has their own personality, considering the size of a patient's body, it is possible to manufacture the auxiliary apparatus for fecal bypass that does not inflict pain on the patient and may prevent damage to the intestinal mucosa and serosa.

To this end, if the numerical value of the auxiliary apparatus for fecal bypass according to the present disclosure is determined in consideration of the size of the anus and the thickness of the intestine of a patient, Equation 1 below may be derived.

$$0<[S-(D+2H)+1.5T] \quad \text{Equation 1}$$

(S: inner diameter of the intestinal tract (mm), H: height of one supporting portion 200 (mm), D: outer diameter of the body part 100 (mm), T: thickness of the intestine (mm))

Since the resistance to intestinal pressure of a patient is determined by the thickness of the intestine, the thickness of the intestine should be considered in order to prevent damage to the intestinal mucosa and serosa. In addition, as a result of performing a plurality of experiments, it was numerically confirmed that the first constant that does not cause damage to the intestinal mucosa and serosa is 5. Further, as a result of considering the thickness of the intestine, it was found that calculating the second constant which is 1.5 for the thickness of the intestine was the largest.

That is, the intestinal mucosa and serosa will not be damaged when determining the outer diameter of the body part 100 and a height of the supporting portion 200 to satisfy the following conditions: a sum obtained by adding up the outer diameter of the body part 100 and the height of the supporting portion 200 of the auxiliary apparatus for fecal bypass of the present disclosure multiplied by 2 is smaller than a sum of adding up a value obtained by multiplying the second constant by the thickness of the intestine and the inner diameter of the intestine, and a value obtained by subtracting a sum of the outer diameter of the body part 100 and a height of one supporting portion 200 multiplied by 2, from the value of adding up the inner diameter and a value obtained by multiplying the second constant by a thickness of the intestine is smaller than a value adding up the first constant and a value of the second constant multiplied by a thickness of the intestine.

However, the above constraints may minimize damage to the mucous membrane of the inner wall of the intestine and the serosal layer, which is the outer layer, but it is insufficient to reduce abdominal pain of patients. Therefore, the present invention is configured to include a liquid moving tube 400.

Conventionally, the pain caused by the increase in intestinal pressure of a patient using the auxiliary apparatus for fecal bypass was not considered. That is, only injecting the treatment liquid into the intestine and closing the intestine was considered. However, as described above, this not only caused abdominal pain in the patient, but also strongly pushed the auxiliary apparatus for fecal bypass toward the anus, and the patient's mucous membrane was damaged.

In order to overcome this, the liquid moving tube 400 according to the present disclosure is configured to allow transfer of the liquid in one direction and transfer in the other direction at the same time. That is, to be able to inject the treatment liquid into the intestine, when the pressure is increased in the intestine and strong pressure is applied to the auxiliary apparatus for fecal bypass of the present invention, extra space is allowed, into which some treatment liquid or a mixture of the treatment liquid and the contents in the intestine may be partially located or transferred.

However, in this case, the liquid moving tube 400 must satisfy the following conditions.

First, the treatment liquid should not be transferred until the internal pressure of the intestine reaches a specific pressure by the peristalsis of the intestine, and when the internal pressure reaches a specific numerical value of pressure, the treatment liquid should be automatically refluxed through the liquid moving tube 400. Second, the treatment liquid should not be obstructed by the contents, and third, even if it is obstructed by the contents in the intestine, the obstructed part should be easily penetrated.

TABLE 6

| | size of a cross-section of the liquid moving tube 400 | | | | | | | |
|---|---|---|---|---|---|---|---|---|
| | 2 | 3 | 4 | 5 | 6 | . . . | 22 | 23 |
| whether liquid reflux is allowed or not | X | ○ | ○ | ○ | ○ | ○ | ○ | ○ |

As a result of performing an experiment by varying the cross section of the liquid moving tube 400 in order to manufacture a liquid moving tube 400 that satisfies the above conditions, the reflux of the treatment fluid was made possible under intestinal pressure that does not cause a patient to feel abdominal pain, when the cross section of the liquid moving tube 400 is 3 $mm^2$ or more. That is, abdominal pain due to peristalsis is reduced from a case where the size of the cross-section of the liquid moving tube 400 is 3 $mm^2$, and when the size of the cross-section of the liquid moving tube 400 is 4 $mm^2$, the reflux flow of the treatment liquid became smooth. Further, since when the size of the cross-section of the liquid pipe 400 was 3 $mm^2$ or more, occlusion of the liquid moving tube 400 due to feces lump did not occur. However, when the size of the cross section of the liquid moving tube 400 is 3 $mm^2$ to 4 $mm^2$ or more, occlusion of the liquid moving tube 400 due to feces lump was occasionally observed, but by injecting a small amount of treatment liquid (about 50 cc or more) to the liquid moving tube 400, the occlusion was easily solved.

However, when the cross section of the liquid moving tube 400 is 3 $mm^2$ to 10 $mm^{2\ or}$ less, the reflux flow of the treatment liquid through the liquid moving tube 400 is allowed, but sometimes the cross section of the liquid moving tube 400 is closed due to the contents in the intestine. However, in this case, when a suction force is applied to the liquid moving tube 400 using a sucking device (e.g., a syringe), a passage of the liquid moving tube 400 is reopened.

When the cross-section of the liquid moving tube 400 is greater than or equal to 17 $mm^2$, it was confirmed that, when the intestines perform peristalsis, the treatment liquid or a mixture of the treatment liquid and the intestinal contents is refluxed.

Therefore, as a result of performing a plurality of experiments, when the cross section of the liquid moving tube 400 is set to 3 $mm^2$ or more to 23 $mm^2$ or less, reflux of the treatment liquid or the mixture in which the treatment liquid and the intestinal contents are mixed was allowed within the range in which the patient does not feel abdominal pain, and even if the liquid moving tube 400 was closed by the contents in the intestine, the passage could be easily opened.

More preferably, in consideration of the intestinal peristalsis, the cross-section of the liquid moving tube 400 should be set to 5 $mm^2$ or more to 20 $mm^2$ or less for natural reflux of the treatment liquid.

In addition, in the present invention, due to the presence of the liquid moving tube 400, when the internal pressure in the intestine is increased due to the peristalsis of the intestine, the washing liquid is refluxed into the liquid moving tube 400, and when the internal pressure in the intestine is decreased, the washing liquid returns into the intestine, thereby the amount of treatment liquid injected into a patient may be dramatically reduced. Further, reflux, decompression and re-injection of the liquid is performed automatically, without help or manipulation of a patient or an assistant.

Since the transfer of the liquid occurs all the time, the contents of the intestine and the washing liquid (treatment liquid) may be mixed well. As a result, time taken for treatment is reduced, and the mucosal damage of the intestinal wall may be reduced because an instance where the body part or supporting portion is pushed by pressure during the treatment period does not occur.

Although the present disclosure has illustrated and described in relation to specific embodiments, it will be obvious to those skilled in the art that the present invention can be variously modified and changed without departing from the technical concept of the present invention provided by the following claims.

The invention claimed is:

1. An auxiliary apparatus for fecal bypass for bypassing and discharging feces in intestines, the auxiliary apparatus comprising:

a main body part being inserted into an anus and positioned on an inside of the intestines;

a set of supporting portions including a supporting portion and a next supporting portion, the supporting portion formed to be spaced apart from the next supporting portion at an interval of 8 mm to 25 mm along an outer periphery of the main body part and fixing the main body part to be positioned at a rectum by expanding and being in close contact with an inner surface of the intestines when air or liquid is injected to the intestines;

a blocking part installed inside the main body part and expanding when the air or the liquid is injected so as to close a space inside the main body part, wherein the liquid includes a treatment liquid; and a liquid moving tube installed inside the main body part to prevent closure of the main body part even if the blocking part is expanded and allowing the treatment liquid injected from an outside of the anus to be injected into the intestines, wherein the liquid moving tube is formed to open an upper portion of the liquid moving tube so that the treatment liquid is injected into the intestines, and automatically adjusts pressure inside the intestines by allowing some reflux of the feces mixed with the treatment liquid through the liquid moving tube in response to the pressure inside the intestines being increased by a peristalsis of the intestines, and wherein a cross section of the liquid moving tube has an area in a range of 3 $mm^2$ to 23 $mm^2$.

2. The auxiliary apparatus for fecal bypass of claim 1, wherein a size of a base of the supporting portion has a base length in a range of 4 mm or more to 15 mm, and wherein a size of an outer diameter of the main body part is in a range of 10 mm to 30 mm.

3. The auxiliary apparatus for fecal bypass of claim 2, wherein a configuration of the auxiliary apparatus for fecal bypass satisfies a formula:

$$0<[S-(D+2H)+1.5T]<[5+1.5T]$$

(wherein S is an internal diameter of an intestinal tract, His a height of the supporting portion, D is the outer diameter of the main body part, and T is a thickness of the intestines).

4. The auxiliary apparatus for fecal bypass of claim 2, further comprising:

an air flow tube communicating with the supporting portion and allowing the supporting portion and the next supporting portion to expand at a same time when the air is injected.

5. The auxiliary apparatus for fecal bypass of claim 1, wherein the main body part is positioned inside the auxiliary apparatus for fecal bypass in a form of a long rod set to facilitate an entry of the main body part into the anus, and an upper part of the auxiliary apparatus includes a cover formed in a round shape and has a symmetrical incision portion with respect to a center.

6. The auxiliary apparatus for fecal bypass of claim 5, wherein the auxiliary apparatus for fecal bypass comprises, in order for the main body part provided inside the cover to separate from the cover, a pusher in a form of a long rod contacting with a lower portion of the main body part and pushing the main body part upward to move the main body part upward and to make a size of an upper portion of the cover to be greatly deformed so as to allow the main body part entering into an inside of the intestines.

* * * * *